US012089547B2

(12) United States Patent
Simpson et al.

(10) Patent No.: US 12,089,547 B2
(45) Date of Patent: Sep. 17, 2024

(54) ENDOPHYTE SCREENING

(71) Applicants: National University Corporation Tottori University, Tottori (JP); Grasslanz Technology Limited, Lincoln (NZ); The Grains Research and Development Corporation, Barton (AU)

(72) Inventors: Wayne Roydon Simpson, Palmerston North (NZ); Richard David Johnson, Palmerston North (NZ); Hisashi Tsujimoto, Tottori (JP)

(73) Assignees: Grasslanz Technology Limited, Lincoln (NZ); National University Corporation Tottori University, Tottori (JP); The Grains Research and Development Corporation, Barton (AU)

(*) Notice: Subject to any disclaimer, the term of this patent is extended or adjusted under 35 U.S.C. 154(b) by 0 days.

(21) Appl. No.: 18/110,056

(22) Filed: Feb. 15, 2023

(65) Prior Publication Data

US 2023/0320310 A1    Oct. 12, 2023

Related U.S. Application Data

(63) Continuation of application No. 16/971,647, filed as application No. PCT/IB2019/051395 on Feb. 20, 2019, now abandoned.

(30) Foreign Application Priority Data

Feb. 21, 2018    (NZ) ........................................ 740055

(51) Int. Cl.
*A01H 17/00*    (2006.01)
*A01N 63/30*    (2020.01)
*C12Q 1/6895*    (2018.01)

(52) U.S. Cl.
CPC ............. *A01H 17/00* (2013.01); *A01N 63/30* (2020.01); *C12Q 1/6895* (2013.01); *C12Q 2600/156* (2013.01)

(58) Field of Classification Search
CPC ...................................................... A01H 17/00
See application file for complete search history.

(56) References Cited

PUBLICATIONS

The National BioResorce Project-WHEAT Material Transfer Agreement downloaded Aug. 1, 2022 5 pages (Year: 2010).*
New Zealand Environment Protection Authority Application Form: To obtain approval to release new organisms, APP202236 Grasslanz Technology Ltd and Ag Research Ltd. 46 pages (Year: 2014).*
Simpson et al Journal of Systematics and Evolution vol. 52, No. 6, pp. 794-806 (Year: 2014).*
Simpson, W. R. (2016) Hordeeae Epichloe endophytes and the formation of synthetic symbioses with cereal grasses. Doctoral Thesis. Massey University.
https://shigen.nig.ac.jp/wheat/komugi/request/nbrpStrainDepositionAction.do; last accessed Nov. 21, 2023.
https://shigen.nig.ac.jp/wheat/komugi/strains/aboutNbrpTacbow.jsp; last accessed Nov. 21, 2023.

* cited by examiner

*Primary Examiner* — David H Kruse
(74) *Attorney, Agent, or Firm* — Lewis Kohn & Walker LLP; David M. Kohn; Kari Moyer-Henry

(57) ABSTRACT

The present invention relates to isolated strains of *Epichloë* endophytes that form stable symbiotic associations with cereal grasses, particularly wheat, wherein the symbiotic associations are combinations of endophytes and host plants that are not found in nature The invention also relates to methods of identifying and/or selecting fungal endophytes that form stable symbiotic associations with wheat plants including methods of screening for fungal endophytes that form stable symbiotic associations with wheat plants, and to methods of screening for wheat plants that form stable symbiotic associations with fungal endophytes.

13 Claims, 1 Drawing Sheet

Specification includes a Sequence Listing.

ENDOPHYTE SCREENING

RELATED APPLICATIONS

This application is a continuation of U.S. patent application Ser. No. 16/971,647 filed Aug. 20, 2020, which is a U.S. National Stage application under 35 U.S.C. § 371 from International Patent Application No. PCT/IB19/51395 filed Feb. 20, 2019, which claims the benefit of priority from New Zealand Patent Application No. 740055 filed Feb. 21, 2018.

REFERENCE TO SEQUENCE LISTING

The Sequence Listing submitted as an XML filed named "1064.202C1.xml," created on Jul. 5, 2023, and having a size of 57 kB is hereby incorporated by reference pursuant to 37 C.F.R. § 1.835(a)(2).

TECHNICAL FIELD

The present invention generally relates to select strains of *Epichloë* fungal endophytes that form stable symbiotic associations with cereal grasses, particularly wheat, to methods of identifying and/or selecting fungal endophytes that form stable symbiotic associations with wheat plants including methods of screening for fungal endophytes that form stable symbiotic associations with wheat plants, and to methods of screening for wheat plants that form stable symbiotic associations with fungal endophytes.

BACKGROUND OF THE INVENTION

Grown worldwide, wheat is one of the oldest and most important cereal crops. Wheat grain is used widely to produce the flour used in a large array of baked goods and for making pasta. Wheat is also used for the production of starch, malt, dextrose, gluten, alcohol and other commercial products. Vegetative portions of wheat plants may be used as straw, or converted to silage, or used for animal fodder, including for in situ grazing.

More cultivable land worldwide is used for wheat production than any other food crop with 2014 production estimates in the neighbourhood of 220 million hectares of wheat sown (UN Food and Agriculture Organization, 2014). Amongst the cereals, wheat production is second only to maize, with about 750 million tonnes of wheat produced in 2016 (UN Food and Agriculture Organization, 2016). Wheat has a protein content of about 13% and is a leading source of human vegetal protein. Whole wheat is a source of essential nutrients and dietary fibre.

As would be expected from such a widely grown agricultural crop, wheat is targeted by many pests, the activities of which can severely reduce overall production. Known pests include, but are not limited to, many Lepidoptera (moths and butterflies) including pink borer and armyworms; aphids including cereal aphids (Homoptera); thrips (Thysanoptera); wireworms, ground beetle (*Zabrus tenebrioides*), cereal leaf beetles (*Oulema melanopus, O. gallaeciana*) and white grubs (Coleoptera); Diptera including leatherjackets (*Tipula* spp.), wheat bulb fly (*Delia coarctata*), leaf miners (*Agromyza* spp.), fruit fly (*Oscinella frit*), stem boring flies (*Diptera*), Hessian fly (*Mayetiola destructor*), saddle gall midge (*Haplodiplosis marginata*); grasshoppers (Orthoptera); termites (Isoptera); nematodes and slugs.

To combat losses in productivity, effective pest protection during cultivation is required to ensure that a good quantity of acceptable quality grain is produced.

Known methods of pest control for wheat include some or all of the following practices: the use of pest resistant cultivars, optimizing time of planting and planting with healthy seeds, effective crop rotation, destruction, and/or burial or removal of crop debris (stubble). Additional methods of pest control that may be required include the use of various pesticides on plants and/or seeds. At times, simultaneous application of two or more active substances may be required for the control of pests.

However, the use of many pesticides can be problematic due to the known problems associated with the chemicals frequently used for such purposes. Many pesticides are toxic and can be dangerous to human and animal consumers of treated agricultural crops (Casida and Quistad, 1998). In particular, the accumulation, in humans and animals of toxic pesticides can lead to serious health issues for individuals, particularly during early development. For example, pesticide exposure has been linked to respiratory disorders, developmental cancers and shown to have lasting effects on the development of mental abilities (Zejda et al. 1993). Many pesticides also kill beneficial organisms that help control pests and that carry out essential ecosystem services such as pollination and nutrient cycling.

The use of pesticides may be difficult to control in variable environmental conditions leading to unwanted dispersal of toxic compounds, for example by drift of sprays or by soil leaching. In addition, the pests may develop pesticide resistance for a number of reasons, including improper practice and handling, which can pose a real threat to crop (grain) yields. Accordingly, there is a need for pest control measures that do not use applied pesticides.

In some crops, particularly forage grasses, fungal endophytes are used to increase plant resistance to certain pests, diseases and abiotic stresses. However, the range of agricultural crops that harbour useful fungal endophyte strains is limited.

Therefore, it is an object of the present invention to provide at least one strain of *Epichloë* fungal endophyte that forms a stable symbiotic association with at least one cereal grass, particularly wheat and/or to provide a method of identifying a fungal endophyte that will form a stable symbiotic association with a wheat plant and confer at least some level of pest protection on the wheat plant and/or to provide a method of identifying a wheat plant that will form a stable symbiotic association with a fungal endophyte wherein the endophyte will confer at least some level of pest protection on the wheat plant and/or to at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In one aspect the invention relates to an isolated strain of *Epichloë* fungal endophyte selected from the group consisting of AR3002 (NRRL #50579), AR3013 (NRRL #67557), AR3060 (NRRL #67592), AR3070 (NRRL #67564) and AR3108 (NRRL #67572), and combinations thereof.

In another aspect the invention relates to a method of identifying a wheat plant that forms a stable symbiotic association with a fungal endophyte comprising artificially inoculating a fungal endophyte into a candidate wheat plant to form a wheat plant/endophyte combination,
propagating the wheat plant/endophyte combination,
obtaining seed from the propagated combination, and
identifying the presence of the endophyte in the seed, and
optionally selecting a wheat plant that is capable of forming a stable symbiotic association with a fungal endophyte.

In another aspect the invention relates to a method of making a stable symbiotic combination comprising a wheat plant and a fungal endophyte comprising artificially inoculating a fungal endophyte into a candidate wheat plant to form a wheat plant/endophyte combination,
propagating the wheat plant/endophyte combination,
obtaining seed from the propagated combination, and
identifying the presence of the endophyte in the seed, and
optionally selecting a stable symbiotic combination comprising the wheat plant and the fungal endophyte.

In another aspect the invention relates to a method of conferring at least some level of pest protection or resistance on a wheat plant comprising artificially infecting a wheat plant with at least one *Epichloë* fungal endophyte wherein the wheat plant/endophyte combination produces at least one metabolite at a level sufficient to confer at least some level of pest protection or resistance on the wheat plant.

In another aspect the invention relates to a method of conferring at least some level of disease protection or resistance on a wheat plant comprising artificially infecting a wheat plant with at least one *Epichloë* fungal endophyte wherein the wheat plant/endophyte combination produces at least one alkaloid at a level sufficient to confer at least some level of disease protection or resistance on the wheat plant.

In another aspect the invention relates to a wheat plant infected with a fungal endophyte wherein the wheat plant is not a natural host of the endophyte, and wherein the wheat plant and the fungal endophyte form a stable symbiotic association.

In another aspect the invention relates to a wheat seed infected with a fungal endophyte wherein the wheat seed is not a natural host of the endophyte, and wherein the wheat seed is capable of germinating and growing into a wheat plant comprising the fungal endophyte in a stable symbiotic association.

In another aspect the invention relates to a method of identifying a wheat germplasm that is compatible with an *Epichloë* endophyte comprising contacting the germplasm with at least one *Epichloë* endophyte, and propagating the germplasm for sufficient time to determine if the endophyte is or will be present in the seed of a wheat plant regenerated from, derived from or grown from the germplasm, wherein the presence of the endophyte in the seed indicates that the wheat germplasm is compatible with the *Epichloë* endophyte.

In another aspect the invention relates to a method of identifying an *Epichloë* endophyte that is compatible with a wheat germplasm comprising contacting the endophyte with at least one wheat germplasm, and propagating the germplasm for sufficient time to determine if the endophyte is or will be present in the seed of a wheat plant regenerated from, derived from or grown from the germplasm, wherein the presence of the endophyte in the seed indicates that the endophyte is compatible with a wheat germplasm.

Other aspects of the invention may become apparent from the following description which is given by way of example only and with reference to the accompanying drawings.

The invention may also be said broadly to consist in the parts, elements and features referred to or indicated in the specification of application, individually or collectively, in any or all combinations of two or more of said parts, elements or features, and where specific integers are mentioned herein that have known equivalents in the art to which the invention relates, such known equivalents are deemed to be incorporated herein as if individually set forth.

BRIEF DESCRIPTION OF THE DRAWINGS

The invention will now be described by way of example only and with reference to the drawings in which.

DETAILED DESCRIPTION OF THE INVENTION

Definitions

Figure 1:
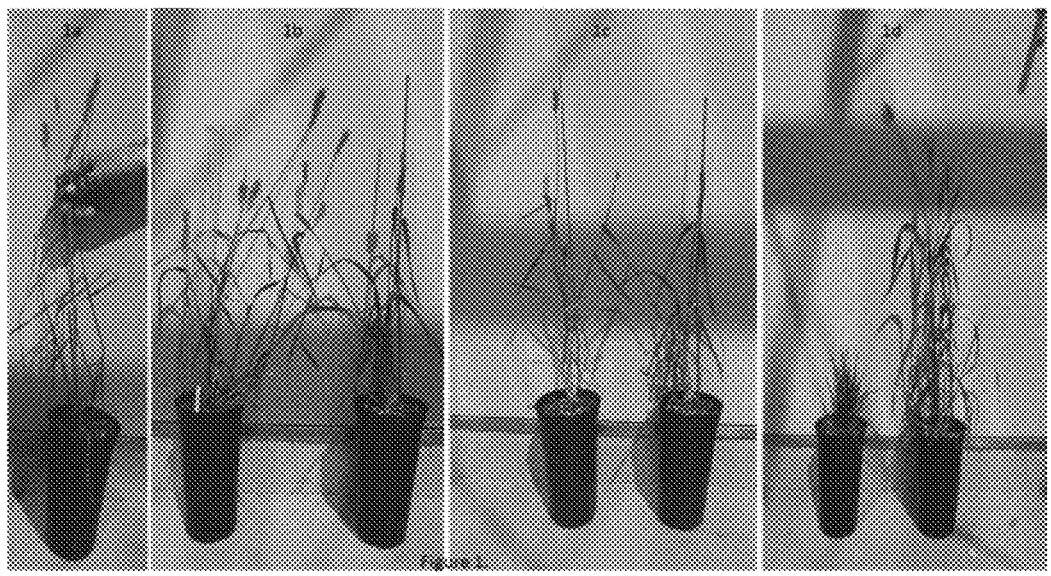
FIG. 1: Symbiotic phenotypes observed in Experiment 2. 1a: Chinese Spring uninfected; 1b: Line TACBOW0236 infected with AR3060 (left) and uninfected (right); 1c: Line TACBOW0059 infected with AR3060 (left) and uninfected (right); 1d: Monad infected (left) and uninfected (right).
Figure 2:
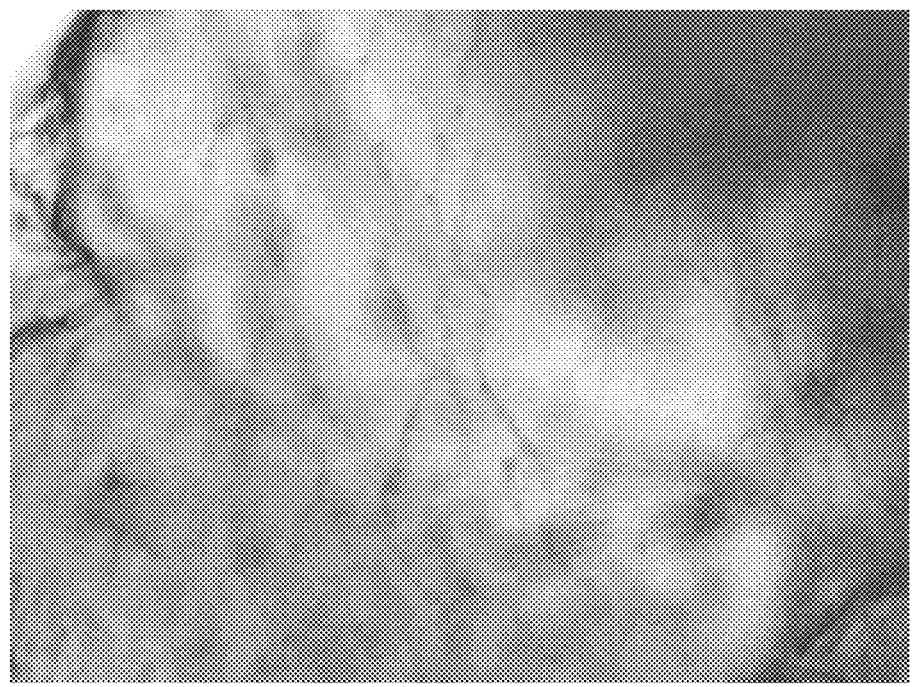
FIG. 2: Seed squash depicting transmission of *Epichloë* endophyte into a wheat grain.

The following definitions are presented to better define the present invention and as a guide for those of ordinary skill in the art in the practice of the present invention.

Unless otherwise specified, all technical and scientific terms used herein are to be understood as having the same meanings as is understood by one of ordinary skill in the relevant art to which this disclosure pertains. Examples of definitions of common terms in botany, microbiology, molecular biology and biochemistry can be found in Biology of Plants, Raven et al. (eds.), W.H. Freeman and Company, (2005); Plant Physiology, Taiz et al. (eds.), Sinauer Associates, Incorporated, (2010); Botany: An Introduction to Plant Biology, J. D. Mauseth, Jones & Bartlett Learning, (2003); Methods for General and Molecular Microbiology, 3rd Edition, C. A. Reddy, et al. (eds.), ASM Press, (2008); Encyclopedia of Microbiology, 2nd ed., Joshua Lederburg, (ed.), Academic Press, (2000); Microbiology By Cliffs Notes, I. Edward Alcamo, Wiley, (1996); Dictionary of Microbiology and Molecular Biology, Singleton et al. (2d ed.) (1994); Biology of Microorganisms $11^{th}$ ed., Brock et al., Pearson Prentice Hall, (2006); Biodiversity of Fungi: Inventory and Monitoring Methods, Mueller et al., Academic Press, (2004); Genes IX, Benjamin Lewin, Jones & Bartlett Publishing, (2007); The Encyclopedia of Molecular Biology, Kendrew et al. (eds.), Blackwell Science Ltd., (1994); Molecular Biology and Biotechnology: a Comprehensive Desk Reference, Robert A. Meyers (ed.), VCH Publishers, Inc., (1995); Symbioses of grasses with seedborne fungal endophytes. Schardl C L et al. (2004) Annual Review of Plant Biology 55: 315-340; and Chemotype diversity of Epichloe, fungal symbionts of grasses, Schardl C L, Young C A, Faulkner J R, Florea S, Pan J (2012) Fungal Ecology 331-344 (Schardl et al., 2012).

It is also believed that practice of the present invention can be performed using standard botanical, microbiological, molecular biology and biochemistry protocols and procedures as known in the art, and as described, for example in Methods of Studying Root Systems, vol. 33, Wolfgang Bahm, Springer-Verlag, (1979); Root methods: A Handbook, Albert L. Smit Springer, (2000); Biodiversity of Fungi: Inventory and Monitoring Methods, Mueller et al., Academic Press, (2004); Environmental Microbiology: Methods and Protocols, J. F. T. Spencer et al., Humana Press, (2004); Environmental Microbiology, P. D. Sharma, Alpha Science International, (2005); Environmental Microbiology, J. R. Leadbetter, Gulf Professional Publishing, (2005), Molecular Cloning: A Laboratory Manual, Maniatis et al., Cold Spring Harbor Laboratory Press, (1982); Molecular Cloning: A Laboratory Manual (2 ed.), Sambrook et al., Cold Spring Harbor Laboratory Press, (1989); Guide to Molecular Cloning Techniques Vol. 152, S. L. Berger and A. R. Kimmerl (Eds.), Academic Press Inc., (1987); Biotechnology of Endophytic Fungi of Grasses. 1994 Bacon and White (Eds.), and other commonly available reference materials relevant in the art to which this disclosure pertains, and which are all incorporated by reference herein in their entireties.

The term "plant" as used herein encompasses whole plants and all parts of a plant from all stages of a plant life cycle including but not limited to vegetative and reproductive cells and tissues, germplasm, propagules, seeds, embryos, shoots, stems, leaves, leaf sheaths and blades, inflorescences, roots, anthers, ligules, palisade, mesophyll, epidermis, auricles, palea, lemma and tillers.

The term "wheat plant" as used herein specifically encompass wheat plant parts, including but not limited to all parts of a wheat plant from all stages of a wheat plant life cycle including but not limited to vegetative and reproductive cells and tissues, germplasm, propagules, seeds, embryos, shoots, stems, leaves, leaf sheaths and blades, inflorescences, roots, anthers, ligules, palisade, mesophyll, epidermis, auricles, palea, lemma and tillers.

The term "alien" when used in reference to a gene, or chromosome or part thereof that is present in a wheat plant means that the gene, or chromosome or part thereof is not naturally present in the wheat plant but has been introduced by artificial manipulation of the wheat plant genetics.

The term, "Epichloë" as used herein refers to a collective group of fungal endophytes previously referred to in the literature as the "epichloae", an endophyte group containing the two previously named genera of fungal endophytes: the members of the anamorphic forms Neotyphodium and the members of the teleomorphic forms Epichloë (Leuchtmann et al., 2014).

The term, "conferring at least some level of pest protection or pest resistance or both" and grammatical variations thereof as used herein encompasses an increase in pest protection or resistance that results in a measurable reduction in the incidence, severity and/or duration of the effects of a pest on a wheat plant, particularly detrimental effects, as compared to a control plant that is a host plant lacking the Epichloë fungal endophyte or a host plant combined with a different fungal endophyte. Preferably a measurable reduction is a statistically significant reduction with a P-value of 0.05 or less.

The terms, "a level sufficient to confer pest protection" and "a level sufficient to confer pest resistance" and grammatical variations thereof as used herein with reference to levels of secondary metabolites, particularly alkaloids, mean any level of a secondary metabolite, particularly an alkaloid, that when produced by a stable plant-endophyte symbiosis, is sufficient to produce a measurable reduction in the incidence, severity or duration of a pest infestation or infection or detrimental effect due to the pest infestation or infection, on a wheat plant that is infected with an Epichloë fungal endophyte according to the invention as compared to a control plant that is a host plant lacking the Epichloë fungal endophyte or a host plant combined with a different fungal endophyte.

Preferably the alkaloid is an Epichloë synthesized alkaloid with demonstrated bioactivity. Preferably the alkaloid is an indole diterpene alkaloid or an ergot alkaloid or peramine or loline or a loline derivative. Preferably a measurable reduction is a statistically significant reduction with a P-value of 0.05 or less.

The term, "has increased resistance to plant disease" and grammatical variations thereof as used herein encompasses measurably reducing the incidence, severity and/or duration of the effects of a plant disease on a host plant as compared to a control plant that is a host plant lacking the Epichloë fungal endophyte or a host plant combined with a different fungal endophyte.

In some embodiments the host plant is a Triticum spp. (wheat) plant, preferably a T. aestivum host plant that is infected with an Epichloë fungal endophyte according to the invention. Preferably a measurable reduction is a statistically significant reduction with a P-value of 0.05 or less.

The terms, "a level sufficient to confer protection from plant disease" and "a level sufficient to confer resistance to plant disease" and grammatical variations thereof as used herein with reference to levels of alkaloids mean any level of an alkaloid produced by the host plant-endophyte symbiosis that is sufficient to produce a measurable reduction in the incidence, severity or duration of a plant disease infestation, infection or detrimental effect on a host plant as compared to a control plant that is a host plant lacking the Epichloë fungal endophyte or a host plant combined with a different fungal endophyte, preferably wherein the host plant is a wheat plant. Preferably the alkaloid is an Epichloë synthesized alkaloid with demonstrated bioactivity. Preferably the alkaloid is an indole diterpene alkaloid or an ergot alkaloid or peramine or loline or a loline derivative. Preferably a measurable reduction is a statistically significant reduction with a P-value of 0.05 or less.

The term "statistically significant" as used herein refers to the likelihood that a result or relationship is caused by something other than random chance. A result may be found to be statistically significant using statistical hypothesis testing as known and used in the art. Statistical hypothesis testing provides a "P-value" as known in the art, which represents the probability that the measured result is due to random chance alone. It is believed to be generally accepted in the art that levels of significance of 5%(0.05) or lower are considered to be statistically significant.

The term, "enhanced pest protection" as used herein refers to a level of pest protection conferred on a wheat plant in stable symbiotic association with an Epichloë fungal endophyte that reduces the incidence, severity and/or duration of a pest infestation, infection or detrimental effect on the wheat plant due to the presence and/or activity of a given pest as compared to the incidence, severity and/or duration of the same pest infestation, infection and/or detrimental effect on a wheat plant lacking a fungal endophyte (a control plant), and/or a wheat plant having a different fungal endophyte.

The terms, "artificially infecting", "artificially inoculating", "artificial inoculation" and other similar grammatical variations mean any inoculation or infection of a plant, particularly a wheat plant, with a fungal endophyte to form a plant/fungal symbiotic association that is not known from nature.

The term "in planta" as used herein in the context of fungal endophytes refers to the endophyte when it is living symbiotically within a host plant. Preferably the fungal endophyte is living in a stable symbiotic association within the host plant.

The terms a "stable symbiosis", "stable symbiotic association" and "stable symbiotic combination", and grammatical variations thereof, mean that the endophyte is vertically transmitted via the normal life cycle of the host plant to the next generation of host plant via seed. Being "vertically transmitted", including to the next generation of host plant via seed, means that the host plant is infected with the endophyte in a first generation and produces seeds which when germinated grow into a second generation of host plants that are also infected with the endophyte.

The term "receptive wheat plant or part thereof" and grammatical variations thereof means a wheat plant or part thereof that is able to be infected by an Epichloë fungal endophyte to form a stable symbiosis.

The term "normal life cycle" as used herein refers to the normal reproductive cycle of wheat, particularly a hexaploid wheat, which includes growth of a first generation of plant to produce seeds which when germinated grow into a second generation of plant.

The term "normal phenotype" of a host plant as used herein refers to the typical morphology, growth and other phenotypic characteristics of the host plant as displayed during the life cycle of the host plant, including the host plant reproductive cycle and host plant seed as known and generally accepted in the art for that host plant when not containing endophyte. In a preferred embodiment, a normal phenotype is a tall floral phenotype.

The term "abnormal phenotype" referring to a host plant as used herein refers to the morphology, growth or other phenotypic characteristics of the host plant at any stage of the host plant life cycle including the host plant reproductive cycle and host plant seed which is different from that known and generally accepted in the art as typical or within the generally observed range for that host plant. The term "abnormal phenotype" referring to a host plant as used herein may include stunted plants or dwarf plants or plants with obvious visual external evidence of endophyte infection or plants failing to complete normal reproduction through seed but is not limited thereto.

The term "comprising" as used in this specification means "consisting at least in part of". When interpreting statements in this specification that include that term, the features, prefaced by that term in each statement, all need to be present but other features can also be present. Related terms such as "comprise" and "comprised" are to be interpreted in the same manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

DETAILED DESCRIPTION

Many cool-season grasses (Poaceae, subfam. Pooideae) possess seed-borne Epichloë fungal endophytes that are known for their bioprotective properties, and especially for production of anti-pest alkaloids such as lolines (Zhang et al., 2010) and peramine (Koulman et al., 2007). Asexual Epichloë (Neotyphodium species) are primarily or entirely transmitted vertically, whereas the sexual structures (stromata) of the related Epichloë species can give rise to horizontally transmissible spores (ascospores) (Zhang et al., 2010).

The majority of Neotyphodium species are considered closely related to species of the genus Epichloë. Many Neotyphodium species may have evolved from Epichloë by processes involving interspecific hybridization (Tsai et al., 1994). Based on molecular phylogenetic evidence, some authors consider that asexual Neotyphodium species are derived either from individual Epichloë species, or from hybrids sharing at least two ancestral Epichloë species (Tsai et al., 1994; Moon et al., 2004). Current taxonomy considers that the members of the anamorphic form genus Neotyphodium are very closely related to members within the teleomorphic genus Epichloë (Glenn et al., 1996). Following previous codes of botanical nomenclature, anamorphic form genus refers to an asexual spore or vegetative state, and a teleomorphic genus refers to the sexual state. Currently the code of botanical nomenclature treats a single fungus with a single naming protocol (Miller et al. 2011). Collectively, the two genera, Neotyphodium and Epichloë, are known in the art as the "Epichloë" endophytes, although these two genera have been merged recently into the single genus, Epichloë (Leuchtmann et al., 2014).

Symbiotic associations between Epichloë fungi and host grasses are common, and molecular phylogenetic evidence suggests that the species specificity observed in these symbiotic associations is due to the co-evolution of these groups of plants and fungal endophytes (Schardl et al., 2008).

No modern domesticated cereals are naturally infected with Epichloë endophytes although some wild type relatives may be (Marshall et al., 1999). Without wishing to be bound by theory, the inventors believe that during the evolution of modern cereals, agricultural practices such as storing seed may have led to the loss of historical associations, if they existed (Welty et al., 1987).

Generally speaking, symbiotic associations formed between host plants and their Epichloë fungal endophytes are based on complex and intimate biological interactions which lead to a high degree of species specificity for both the endophyte and host (Simpson and Mace, 2012).

Accordingly, establishment of a stable plant/fungal symbiosis between an Epichloë fungal endophyte and a host plant that is not a natural host for the fungus is both problematic and unpredictable (Simpson and Mace, 2012). Of note, modern wheat cultivars do not naturally harbour Epichloë endophytes. As the skilled artisan will appreciate endophytes are host specific and it is difficult to move endophytes between different host species.

This is thought to be due to the requirement, in the formation of such symbioses, for successful integration of multiple biological variables between partners which can include ecological, biochemical and/or molecular incompatibilities (Christensen et al., 2000). The present disclosure details the large volume of research required, including significant trial and error experimentation, to develop successful protocols and procedures by which stable symbiotic associations between certain strains of Epichloë fungal endophytes and wheat plants that are not the natural hosts for such fungi have been established.

Surprisingly, the inventors have determined that artificial inoculation can be used to establish stable symbioses between some Epichloë fungal endophytes and wheat plants, particularly hexaploid wheat plants. Through the use of the inventive methods described herein, the inventors are able to produce infected wheat plants that form a stable symbiotic association with the infecting fungus allowing the infected plant to progress through a normal life cycle, particularly that produce a tall floral phenotype that progresses through a normal life cycle including producing seed containing the endophyte that is able to germinate to form an infected next generation of the host plant.

Additionally, the inventors have found that methods disclosed herein can identify symbiotic associations that can provide at least some level of benefit to the host plant in terms of the production in the plant of at least one metabolite, preferably at least one secondary metabolite, preferably an alkaloid, that may confer at least some level of pest protection or resistance and/or at least some level of disease protection or resistance to the host plant, particularly a wheat host plant. Of particular interest are stable symbiotic associations that produce at least one loline alkaloid, loline alkaloid derivative, indole diterpene alkaloid, peramine or ergot alkaloid or a combination thereof. Also, of particular interest in this invention are stable symbiotic associations that produce at least one secondary metabolite, preferably at least one alkaloid, wherein the association does not produce known mammalian toxins, preferably ergovaline and/or lolitrem B.

This has meant similar efforts to introduce Epichloë endophytes into modern wheat, which do not naturally harbour endophytes, have struggled in creating a stable combination, where the resulting combination often shows a compromised phenotype, particularly in its stature and reproductive ability. This has meant that resulting combinations are stunted in stature and often do not set seed, or if seeds are made, they are visibly less healthy, appearing shrivelled.

The inventors have surprisingly determined that certain fungal endophyte isolates taken from wild relatives of cereals are suitable for establishing stable plant/fungal symbioses with wheat plants. In particular, the inventors have established stable symbiotic associations that result in an Epichloë fungal endophyte/wheat plant combination that may have at least some level of enhanced pest protection or resistance as compared to wheat control plants; i.e., plants of the same wheat species or line that are un-infected with the same symbiotic Epichloë fungal strain. Without wishing to be bound by theory, the inventors believe that enhanced pest protection or resistance is to be expected in fungal endophyte/host plant combinations that produce certain secondary metabolites, particularly alkaloids, particularly loline, loline derivatives, indole diterpenes, ergot alkaloids and/or peramine. For example, certain fungal endophyte/host plant combinations are expected to produce peramine, N-acetylnorloline, loline, N-formylloline, N-acetylloline and/or N-methylloline, but not limited thereto. Other fungal endophyte/host plant combinations are expected to produce other metabolites, particularly secondary metabolites that have previously demonstrated bioactivity. In one non-limiting example such secondary metabolites may be alkaloids. Preferably such alkaloids are not ergovaline, lolitrem B or derivatives or variants of these alkaloids that have previously demonstrated mammalian toxicity.

The inventors believe that the production of secondary metabolites, particularly alkaloids, particularly indole diterpenes and/or loline and/or peramine and/or ergot alkaloid(s) by the Epichloë fungal endophyte or the fungal endophyte/host plant combination provides at least some level of enhanced pest protection and/or increased disease resistance to the host plant. In particular, following from the use of the inventive methods disclosed herein, the inventors anticipate that wheat plants, particularly hexaploid wheat plants, particularly T. aestivum spp. host plants, infected with certain strains of Epichloë fungal endophyte will have enhanced protection against a variety of pests, including insect pests, as compared to wheat control plants.

As a result of a lengthy research program, the applicants have identified for the first time, Epichloë fungi that form stable plant/fungal symbioses with wheat plants and have established that these and other Epichloë fungi can be used in methods of screening wheat plants for endophyte compatibility and/or for identifying and/or selecting wheat plants that will form stable symbioses with an Epichloë.

The applicants have further identified endophytes capable of conferring to an infected wheat host plant, when in symbiosis with that plant, the ability to produce one or more alkaloids known to provide at least some level of enhanced pest protection to the plant, as compared to an un-infected control plant. In particular, the one or more alkaloids may be loline, loline derivatives or peramine alkaloids.

In one aspect the invention relates to an isolated strain of Epichloë fungal endophyte selected from the group consisting of AR3002 (NRRL #50579), AR3013 (NRRL #67557), AR3060 (NRRL #67592), AR3070 (NRRL #67564) and AR3108 (NRRL #67572), and combinations thereof. Also described herein is the isolated strain of Epichloë fungal endophyte: AR3067 (NRRL #50719).

Fungal endophyte strains AR3002, AR3013, AR3060, AR3067, AR3070 and AR3108 were deposited at The United States Department of Agriculture, Agricultural Research Service Midwest Area, National Center for Agricultural Utilization Research, 1815 North University Street, Peoria, Illinois, 61604-3902, USA on the dates shown below for strains:

AR3002 (NRRL #50579) on 13 Oct. 2011
AR3013 (NRRL #67557) on 5 Feb. 2018
AR3060 (NRRL #67592) on 5 Feb. 2018
AR3067 (NRRL #50719) on 6 Mar. 2012
AR3070 (NRRL #67592) on 5 Feb. 2018, and
AR3108 (NRRL #67572) on 5 Feb. 2018 according to the Budapest Treaty for purposes of patent procedure.

AR3067 was first deposited in relation to PCT/IB2014/059479, the entirety of which is incorporated by reference herein.

The endophytes were isolated from Elymus spp., including E. mutabilis, E. dahuricus, E. dahuricus sub species excelsus, E. elymoides sub species brevifolius and/or E. uralensis obtained from locations in Canada, China, Kyrgyzstan, Kazakhstan, the USSR and Russia as described in PCT IB/2014/059479.

Endophytes were isolated from the plants following surface sterilisation of plant tissue as described by Christensen et al. (2002).

Once isolated, the isolated and/or biologically pure fungal endophyte may be cultured using standard techniques as known in the art and as disclosed herein, including in the examples.

In one embodiment the isolated strain of *Epichloë* endophyte comprises at least one SSR allele selected from the group consisting of ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095 as shown by strain in Table 2, wherein the at least one SSR allele has the number of base pairs (bp) as shown in Table 2, ±0.8 bp.

In one embodiment the isolated strain of *Epichloë* endophyte comprises at least two SSR alleles, preferably at least 3, at least 4, at least 5, at least 6, at least 7, at least 8, at least 9, at least 10, at least 11, at least 12, at least 13, at least 14, at least 15, at least 16, at least 17, at least 18, at least 19 additional SSR alleles, preferably 20 SSR alleles as shown by strain in Table 2, wherein each of the additional SSR alleles has the number of base pairs (bp) as shown in Table 2, ±0.8 bp.

In one embodiment the isolated strain of *Epichloë* endophyte comprises the following 22 SSR alleles: B10, B11, ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095 as shown by strain in Table 2, wherein the 22 SSR alleles have the number of base pairs (bp) as shown in Table 2, ±0.8 bp.

In another aspect the invention relates to a stable symbiotic combination comprising an isolated *Epichloë* fungal endophyte selected from the group consisting of AR3002 (NRRL #50579), AR3013 (NRRL #67557), AR3060 (NRRL #67592), AR3067 (NRRL #50719), AR3070 (NRRL #67564) and AR3108 (NRRL #67572), and combinations thereof.

Accordingly, in another aspect the invention relates to a method of identifying a wheat plant that forms a stable symbiotic combination with a fungal endophyte comprising
    artificially inoculating a fungal endophyte into a candidate wheat plant to form a wheat plant/endophyte combination,
    propagating the wheat plant/endophyte combination,
    obtaining seed from the propagated combination, and
    identifying the presence of the endophyte in the seed, and
    optionally selecting a wheat plant that is capable of forming a stable symbiotic combination with a fungal endophyte.

In one embodiment the fungal endophyte is an *Epichloë* fungal endophyte. In one embodiment the *Epichloë* fungal endophyte was isolated from wild cereal grasses, preferably *Elymus* spp. grasses and/or *Hordeum* species grasses. In one embodiment the *Epichloë* fungal endophyte was isolated from a genus within the grass tribe Hordeeae (Triticeace). In one embodiment the *Epichloë* fungal endophyte is a species or strain of *Epichloë* bromicola or a hybrid strain of *E. bromicola* and another *Epichloë* species.

In one embodiment the fungal endophyte is a fungal endophyte isolated from *Elymus* spp. Preferably the fungal endophyte is AR3002 isolated from *E. dahuricus, E. dahuricus* sub species *excelsus*, and/or *E. uralensis*.

In one embodiment the *Epichloë* fungal endophyte strain is selected from the group consisting of AR3002 (NRRL #50579), AR3013 (NRRL #67557), AR3060 (NRRL #67592), AR3067 (NRRL #50719), AR3070 (NRRL #67564) and AR3108 (NRRL #67572), and combinations thereof.

In one embodiment the isolated strain is AR3002.
In one embodiment the isolated strain is AR3013.
In one embodiment the isolated strain is AR3060.
In one embodiment the isolated strain is AR3067.
In one embodiment the isolated strain is AR3070.
In one embodiment the isolated strain is AR3108.

In one embodiment the wheat plant comprises chromosome modifications that increase the compatibility of the wheat plant with an *Epichloë* endophyte infection.

Ultimately the combination of the wheat plant and *Epichloë* fungal endophyte in a stable symbiotic association is selected that produces secondary metabolites, preferably alkaloids such as lolines, peramines, indole diterpenes, or other pesticidal alkaloids that provide deterrence against pests and diseases, abiotic stress protection and as such also have the potential to provide future-proofing of various crops against the effects of climate change.

In another embodiment the wheat plant is a plant from a line obtained from the Tottori Alien Chromosome Bank of Wheat (TACBOW) selected from the group consisting of TACBOW0003 (KCTC 15349BP), TACBOW0005 (KCTC 15350BP), TACBOW0010 (KCTC 15351BP), TACBOW0011 (KCTC 15352BP), TACBOW0018 (KCTC 15353BP), TACBOW0028 (KCTC 15354BP), TACBOW0044 (KCTC 15355BP), TACBOW0045 (KCTC 15356BP), TACBOW0054 (KCTC 15357BP), TACBOW0059 (KCTC 15358BP), TACBOW0067 (KCTC 15359BP), TACBOW0128 (KCTC 15360BP), TACBOW0209 (KCTC 15361BP), TACBOW0221 (KCTC 15362BP), TACBOW0226 (KCTC 15363BP), TACBOW0236 (KCTC 15364BP), TACBOW0237 (KCTC 15365BP), TACBOW0244 (KCTC 15366BP), TACBOW0260 (KCTC 15367BP), TACBOW0261 (KCTC 15368BP), TACBOW0272 (KCTC 15369BP), and TACBOW0275 (KCTC 15370BP).

Under certain conditions, fungal endophytes that are obligate symbionts of one host plant species or strain may be introduced to different host plant species or strain to form a combination that is not normally found in nature. However, such combinations can be unstable and result in host plants having an abnormal phenotype, i.e., abnormal morphological and/or physiological features as compared to host plants of the same line/cultivar or species that are either uninfected or that comprise a naturally occurring symbiont. Abnormal phenotypic features can include dwarf plants (Simpson and Mace, 2012; Simpson et al. 2014), plants with conspicuous epiphytic growth (Christensen et al., 2012), vascular bundle colonisation (Christensen et al., 2001) and localised cell death (Christensen, 1995).

The applicant is the first to provide a stable symbiotic combination between wheat plants and *Epichloë* fungal endophytes that results in a stable plant/fungal combination that shows no abnormal effects of endophyte infection. Stable symbiotic combinations provided herein can exhibit a normal morphological phenotype. In some embodiments a stable symbiotic combination exhibits a normal morphological phenotype that is a tall floral phenotype as described herein. In some embodiments a stable symbiotic combination exhibits a tall floral phenotype that has a complete and normal reproductive cycle.

In one embodiment the wheat plant in the combination shows a normal morphological phenotype. In one embodiment the normal morphological phenotype is a tall floral phenotype that produces seed containing the endophyte. In one embodiment the seed is viable. In one embodiment the seed will germinate to form a next generation of the combination.

In one embodiment the wheat plant/endophyte combination produces at least one secondary metabolite, preferably at least one alkaloid that confers at least some level of pest protection or resistance, or disease protection or resistance, on the combination. In one embodiment the alkaloid is selected from the group consisting of lolines, peramine, indole diterpene alkaloids and ergot alkaloids.

In one embodiment the alkaloid is selected from the group consisting of peramine, N-acetylnorloline, loline, N-formylloline, N-acetylloline and N-methylloline.

In one embodiment the alkaloid confers at least some level of pest protection or pest resistance on the plant/endophyte combination.

In one embodiment the alkaloid confers at least some level of disease protection or disease resistance on the wheat plant/endophyte combination.

In one embodiment the alkaloid is produced at a level sufficient to confer pest protection or pest resistance to the wheat plant/endophyte combination.

In one embodiment the alkaloid is produced at a level sufficient to confer protection or resistance to wheat plant disease to the plant/endophyte combination.

In one embodiment the wheat plant/endophyte combination has increased resistance to pests or increased resistance to plant disease or both, as compared to a wheat plant that is not infected with an *Epichloë* endophyte.

In one embodiment the wheat plant/endophyte combination has increased resistance to pests, wherein the pests are selected from the group consisting of: (1) species of aphids selected from the group consisting of *Rhopalosiphum padi, Schizaphis graminum, Rhopalosiphum maidis, Metopoliphium dirhodum, Sitobion* spp., *Sitobion avenae, Sitobion fragariae,* and *Diuraphis noxis*; (2) species of grass and cereal flies selected from the group consisting of *Oscinella frit, Oscinella pusilla, Mayetiola destructor, Cerodontha* spp., *Cerodontha australis, Cerodontha angustipennis, Formia fumigata, Meromyze americana, Haplodiplosis marginata, Chlorops pumilionis, Tipula* spp. *Chromatomyia fuscula, Cephus pygmaeus, Chromatomyia fuscula,* and *Contarinia tritici*; (3) species of thrips selected from the group consisting of *Limothrips cerealium, Limothrips denticornis, Aptinothrips rufus,* and *Stenothrips graminum*; (4) species of grasshoppers and crickets selected from the group consisting of *Locusta migratoria, Phaulacridium marginale, Phaulacridium vittatum, Melanoplus* spp., and *Teleogryllus commodus*; (5) species of bugs *Nyssius huttoni* or *Blissus leucopertus leucopertus*; (6) weevils of *Sphenophorus* spp. or *Listronotus* spp., including *Listronotus bonariensis* (Argentine stem weevil); (7) species of armyworm, cutworm and leafrollers selected from the group consisting of *Pseudaletia unipuncta, Spodoptera* spp., *Mythimna separata; Persectania aversa, Agrotis ipsilon* and *Epiphyas postvittana*; (8) *Oulema melanopus* leaf bugs; (9) species of white grubs selected from the group consisting of *Popillia japonica, Costelytra giveni* (formerly *C. zealandica*), *Phyllopertha* spp., *Rhizotrogus majalis,* and *Anisoplia segetum*; (10) species of mealybug selected from the group consisting of *Phenacoccus hordei, Balanococcus poae. Ripersella rumicis,* and *Porphyrophora tritici*; (11) species of wireworms *Conoderus* spp., or *Limonius* spp.; (12) *Zabrus tenebrioides* beetles: (13) species of mites selected from the group consisting of *Penthaleus* spp., *Halotydeus destructor,* and *Aceria* spp.; (14) species of stored product pests selected from the group consisting of *Sitophilus oryzae, Sitophilus granarius, Sitotroga cerealella, Rhyzopertha dominica, Cryptolestes* spp., *Oryzaephilus surinamensis, Cadra cautella, Plodia interpunctella, Tribolium confusum, Tribolium castaneum,* and *Lasioderma erricorne*; (15) *Philaenus spumarius* froghoppers; (16) species of nematodes selected from the group consisting of root lesion nematodes of *Pratylenchus* spp. selected from the group consisting of *P. thornei, P. crenatus, P. neglectus* and *P. penetrans*, cereal cyst nematodes of *Heterodera* spp. and *Punctodera* spp. selected from the group consisting of *H. avenae, H. latipons, H. hordecalis, H. filipjevi, H. mani, H. bifenestra, H. pakistanensis* and *P. punctata*, root knot nematodes of *Meloidogyne* spp. selected from the group consisting of *M. chitwoodi, M. naasi, M. artiellia, M. microtyla, M. ottersoni, M. graminicola, M. graminis, M. kikuyensis* and *M. spartinae*, stem nematodes of *Ditylenchus* spp. selected from the group consisting of *D. dipsicai* and *D. radicicola*; and the seed gall nematode *Anguina tritici*; (17) species of slugs selected from the group consisting of *Deroceras reticulatum, Arion hortensis* agg. and *A. subfuscus.*

In one embodiment the pests are nematodes, preferably root lesion nematodes (*Pratylenchus* spp.).

In one embodiment the pests are *Listronotus bonariensis* (Argentine stem weevil).

In one embodiment the wheat plant/endophyte combination has increased resistance to plant disease, wherein the plant disease is caused by a plant pathogen selected from the group consisting of Barley yellow dwarf virus (Leteovirus), wheat soil-borne mosaic virus (Furovirus) and wheat streak mosaic virus (Tritimovirus), *Xanthomonas campestris, Pseudomonas syringae, Colletotrichum graminicola, Glomerella graminicola* [teleomorph], *Alternaria* spp., *Cladosporium herbarum, Mycosphaerella tassiana* [teleomorph], *Epicoccum* spp., *Sporobolomyces* spp., *Stemphylium* spp., *Bipolaris sorokiniana, Cochliobolus sativus* [teleomorph], *Fusarium* spp., *Tilletia caries, Tilletia tritici, Tilletia laevis, Tilletia foetida, Hymenula cerealis, Cephalosporium gramineum, Helminthosporium sativum, Cochliobolus sativus* [teleomorph], *Coprinus sychromorbidus, Dilophospora alopecuri, Tilletia controversa, Claviceps purpurea, Sphacelia segetum* [anamorph], *Fusarium culmorum, Pseudoseptoria donacis, Selenophoma donacis, Neovossia indica, Tilletia indica, Puccinia recondita, Aecidium clematidis* [anamorph], *Cercosporidium graminis, Scolicotrichum graminis, Phaeosphaeria herpotrichoides, Leptosphaeria herpotrichoides, Ustilago tritici, Microdochium nivale, Fusarium nivale, Monographella nivalis* [teleomorph], *Erysiphe graminis, Pythium aphanidermatum, Pythium arrhenomanes, Pythium debaryanum, Pythium graminicola, Pythium ultimum, Gibberella zeae, Fusarium graminearum* [anamorph], *Septoria secalis, Septoria tritici, Mycosphaerella graminicola* [teleomorph]. *Rhizoctonia cerealis, Rhizoctonia solani, Rhizoctonia zeae, Blumeria* spp., *Ceratobasidium cereale* [teleomorph], *Myriosclerotinia borealis, Sclerotinia borealis, Typhula idahoensis, Typhula incarnate, Typhula ishikariensis, Typhula ishikariensis* var. *canadensis, Stagonospora nodorum, Septoria nodorum, Phaeosphaeria nodorum* [teleomorph], *Leptosphaeria nodorum, Urocystis occulta, Puccinia graminis, Aspergillus* spp., *Nigrospora* spp., *Penicillium* spp., *Rhizopus* spp., *Pseudocercosporella herpotrichoides, Tapesia acuformis* [teleomorph], *Uredo glumarum* [anamorph], *Pyrenophora tritici-repentis, Drechslera tritici-repentis* [anamorph], *Helminthosporium tritici-repentis, Puccinia triticina, Pythium* spp., *Rhynchosporium secalis, Puccinia striiformis, Gaeumannomyces graminis, Magnaporthe oryzae* and *Fusarium pseudograminearum.*

Preferably the plant pathogen is *Puccinia recondita, Puccinia triticina, Puccinia graminis, Fusarium* spp., *Pythium* spp., *Rhynchosporium secalis*, *Puccinia striiformis*, *Gaeumannomyces graminis*, or *Fusarium pseudograminearum*.

In one embodiment propagating the wheat plant/endophyte combination through at least one generation comprises propagating the wheat plant/endophyte combination until the endophyte is vertically transmitted from the first generation of the wheat plant to a second generation of the wheat plant. In one embodiment, vertical transmission is by propagule, floral tiller or seed. In one embodiment vertical transmission is by floral tillers and subsequently produced seed. Preferably vertical transmission is by seed.

In one embodiment propagating the wheat plant/endophyte combination through at least one generation comprises growing the wheat plant/endophyte combination until it produces seeds.

In one embodiment propagating is for sufficient time to determine if the endophyte is or will be present in the seed of the wheat plant. In one embodiment the method comprises a step of, after determining if the endophyte is or will be present in the seed of the wheat plant, selecting the endophyte as an endophyte that forms stable symbioses with wheat.

In one embodiment identifying comprises determining that the endophyte is present in the seed using metabolic, genetic or morphological criteria.

In one embodiment the morphological criteria comprise visualizing the endophyte in a seed squash prepared from the seed.

In one embodiment selecting a wheat plant comprises germinating and growing the seed to obtain a second generation wheat plant, identifying that the second generation wheat plant is a stable symbiotic association comprising the candidate endophyte, and selecting the candidate endophyte as an endophyte that forms a stable symbiotic association in a wheat plant.

In one embodiment selecting a wheat plant comprises selecting a fungal endophyte-wheat plant combination that produces at least one secondary metabolite at a level sufficient to confer at least some level of pest protection, pest resistance, disease protection or disease resistance or a combination thereof on the wheat plant. Preferably the secondary metabolite is an alkaloid.

In one embodiment the at least one alkaloid is selected from the group consisting of lolines, peramine, indole diterpenes and ergot alkaloids.

In one embodiment the at least one alkaloid is selected from the group consisting of peramine, N-acetylnorloline, loline, N-formylloline, N-acetylloline and N-methylloline.

In another aspect the invention relates to a method of making a stable symbiotic combination comprising a wheat plant and a fungal endophyte comprising
    artificially inoculating a fungal endophyte into a candidate wheat plant to form a wheat plant/endophyte combination,
    propagating the wheat plant/endophyte combination,
    obtaining seed from the propagated combination, and
    identifying the presence of the endophyte in the seed, and
    optionally selecting a stable symbiotic combination comprising the wheat plant and the fungal endophyte.

In one embodiment selecting a stable symbiotic combination comprises germinating and growing the seed to obtain a second generation wheat plant, identifying that the second generation wheat plant is a stable symbiotic association comprising the candidate endophyte, and selecting the stable combination.

In one embodiment selecting comprises selecting a stable symbiotic combination that produces at least one secondary metabolite at a level sufficient to confer at least some level of pest protection, pest resistance, disease protection or disease resistance or a combination thereof on the wheat plant. Preferably the secondary metabolite is an alkaloid.

In one embodiment the at least one alkaloid is selected from the group consisting of lolines, peramine, indole diterpenes and ergot alkaloids.

In one embodiment the at least one alkaloid is selected from the group consisting of peramine, N-acetylnorloline, loline, N-formylloline, N-acetylloline and N-methylloline.

Contemplated herein as specific embodiments of this aspect of the invention relating to a method of making a stable symbiotic combination are all of the embodiments set out above relating to the other aspects of the invention that are an isolated strain of *Epichloë* fungal endophyte and a method of identifying a wheat plant that forms a stable symbiotic association with a fungal endophyte, including but not limited to particular *Epichloë* fungal endophytes, wheat plants, wheat plant/endophyte combinations, secondary metabolites, and alkaloids produced by wheat plant/endophyte combinations, all as described herein.

In another aspect the invention relates to a method of conferring at least some level of pest protection or resistance on a wheat plant comprising artificially infecting a wheat plant with at least one *Epichloë* fungal endophyte wherein the wheat plant/endophyte combination produces at least one alkaloid at a level sufficient to confer at least some level of pest protection or resistance on the wheat plant.

In another aspect the invention relates to a method of conferring at least some level of disease protection or resistance on a wheat plant comprising artificially infecting a wheat plant with at least one *Epichloë* fungal endophyte wherein the wheat plant/endophyte combination produces at least one alkaloid at a level sufficient to confer at least some level of disease protection or resistance on the wheat plant.

"Artificially inoculating" or "artificially infecting" a wheat plant according to any of the method aspects of the invention may be carried out using whole plants, or parts thereof including germplasm. In one embodiment, artificially inoculating comprises inoculating wheat seedlings that have been germinated for about two weeks. Preferably the seedlings have been germinated for 4 to 9 days.

Outside of this range, seedlings may still form effective associations but in some cases may be too young or too old for establishment of the fungal endophyte. Seeds need to be free of non-target fungi and bacteria to ensure that the seedlings are not overcome by microbial contamination.

In one embodiment, artificial inoculation may be carried out using basal inoculation of wheat seedlings. To effectively establish the fungal symbiont/wheat plant association, inoculation of the endophyte should be made into the wheat plant meristem by incision of the plant and insertion of cultured fungal mycelium.

Contemplated herein as specific embodiments of these aspects of the invention relating to a method of conferring at least some level of pest or disease protection or resistance on a wheat plant are all of the embodiments set out above relating to the other aspects of the invention that are an isolated strain of *Epichloë* fungal endophyte, a method of identifying a wheat plant that forms a stable symbiotic association with a fungal endophyte and a method of making a stable symbiotic combination, including but not limited to particular *Epichloë* fungal endophytes, wheat plants, wheat plant/endophyte combinations, secondary metabolites, and alkaloids produced by wheat plant/endophyte combinations, all as described herein.

It is known to those familiar in the arts of natural pest resistance and protection of grasses that *Epichloë* endophytes growing symbiotically with host grass plants may confer upon the combination some protection from pests. In particular it is known that loline alkaloids and the alkaloid peramine confer some such protection without notable or known toxicity to mammals or humans consuming the grass or products derived indirectly from consumption of the grass.

Lolines are a group of related bioactive natural products which share distinct chemical and biological characteristics. Lolines are alkaloids, i.e. organic compounds containing basic nitrogen atoms and are chemically defined as saturated 1-aminopyrrolizidines with an internal ether bridge joining two ring (C-2 to C-7) carbons. The internal ether bridge, which is uncommon in organic compounds, is considered a signature feature of the group. The specific lolines include norloline and derivatives of its 1-amino moiety being loline (with a methyl group), N-methylloline (with two methyl groups, NML), N-acetylnorloline (with an acetyl group, NANL), N-acetylloline (with a methyl group and an acetyl group, NAL) and N-formylloline (with a formyl group, NFL) (Schardl et al., 2007; Schardl et al., 2012).

Lolines are known to be generally pesticidal and pest-deterring compounds produced in grasses infected by endophytic *Epichloë* fungal symbionts (*Epichloë/Neotyphodium* spp.). Lolines have been shown to increase resistance of the host grass plants to pest herbivory (Bush et al., 1997). The specific lolines may have some variations in the bioactivities against specific pests. It has also been suggested that the presence of lolines may provide a host plant with some level of protection from environmental stresses including drought and spatial competition (Malinowski and Belesky, 2000).

Loline alkaloids are produced in the symbiotic combination by the fungal endophyte. What is important is the production of loline alkaloids by the combination, where the production is induced in the combination by the presence of the fungal endophyte on or within the plant tissues, particularly by the presence of fungal hyphae between plant cells. Historically, the reproduction of the conditions experienced in symbiosis to allow the production of loline alkaloids in vitro was found to be extremely difficult (Porter 1994). It was therefore unknown, until relatively recently, if the loline alkaloids observed to be produced in these symbiotic associations were produced by the fungal endophyte itself, or if they were synthesized in the plant in response to infection. Only relatively recent work by Blankenship et al. (2001) has demonstrated that the endophyte *Neotyphodium uncinatum* can produce lolines in chemically defined growth media. This work suggests that the endophyte is also the producer of the lolines in its naturally occurring host grass (Blankenship et al., 2001). Direct chemical analysis of naturally occurring *Epichloë* also demonstrates this effect (Schardl et al., 2007).

Peramine (a pyrrolopyrazine alkaloid) is a bioactive alkaloid produced by some combinations of endophytes and plants (Schardl et al., 2012). Peramine production has been shown to be dependent upon the functioning of at least one gene of endophyte origin (Tanaka et al., 2005). Peramine has been shown to be a feeding deterrent of some insects which cause damage to plants and can confer protection against infestation of endophyte-infected plants by some insects (Rowan and Latch, 1994).

In another aspect the invention relates to a wheat plant infected with a fungal endophyte wherein the wheat plant is not a natural host of the endophyte, and wherein the wheat plant and the fungal endophyte form a stable symbiotic association.

In one embodiment the wheat plant is a receptive wheat plant wherein the receptive wheat plant is not a natural host of the endophyte, and wherein the receptive wheat plant and the fungal endophyte form a symbiotic association that allows the endophyte to be vertically transmitted to the next generation via seed.

In another aspect the invention relates to a wheat seed infected with a fungal endophyte wherein the wheat seed is not a natural host of the endophyte, and wherein the wheat seed is capable of germinating and growing into a wheat plant comprising the fungal endophyte in a stable symbiotic association.

In one embodiment the fungal endophyte is an *Epichloë* fungal endophyte.

In one embodiment the wheat seed is a seed from a receptive wheat plant.

Contemplated herein as specific embodiments of the aspects of the invention relating to a wheat plant infected with a fungal endophyte and a wheat seed infected with a fungal endophyte are all of the embodiments set out above relating to the other aspects of the invention that are an isolated strain of *Epichloë* fungal endophyte, a method of identifying a wheat plant that forms a stable symbiotic association with a fungal endophyte, a method of making a stable symbiotic combination and methods of conferring at least some level of pest or disease protection or resistance, including but not limited to particular *Epichloë* fungal endophytes, wheat plants, wheat plant/endophyte combinations, secondary metabolites, and alkaloids produced by wheat plant/endophyte combinations, all as described herein.

In another aspect the invention relates to a method of identifying a wheat germplasm that is compatible with an *Epichloë* endophyte comprising contacting the germplasm with at least one *Epichloë* endophyte, and propagating the germplasm for sufficient time to determine if the endophyte is or will be present in the seed of a wheat plant regenerated from, derived from or grown from the germplasm, wherein the presence of the endophyte in the seed indicates that the wheat germplasm is compatible with the *Epichloë* endophyte.

In one embodiment contacting comprises infecting the germplasm with at least one *Epichloë* endophyte.

In one embodiment the method comprises selecting the identified wheat germplasm.

In another aspect the invention relates to a method of identifying an *Epichloë* endophyte that is compatible with a wheat germplasm comprising contacting the endophyte with at least one wheat germplasm, and propagating the germplasm for sufficient time to determine if the endophyte is or will be present in the seed of a wheat plant regenerated from, derived from or grown from the germplasm, wherein the presence of the endophyte in the seed indicates that the endophyte is compatible with a wheat germplasm.

In one embodiment contacting comprises infecting the germplasm with at least one *Epichloë* endophyte.

In one embodiment the method comprises selecting the identified endophyte.

Contemplated herein as specific embodiments of the invention relating to a method of identifying a wheat germplasm that is compatible with an *Epichloë* endophyte and to a method of identifying an *Epichloë* endophyte that is compatible with a wheat germplasm are all of the embodiments set out above relating to the other aspects of the invention that are an isolated strain of *Epichloë* fungal endophyte, a method of identifying a wheat plant that forms a stable symbiotic association with a fungal endophyte, a method of making a stable symbiotic combination, methods of conferring at least some level of pest or disease protection or resistance, and a wheat plant or wheat seed infected with a fungal endophyte, including but not limited to particular *Epichloë* fungal endophytes, wheat plants, wheat plant/endophyte combinations, secondary metabolites, and alkaloids produced by wheat plant/endophyte combinations, all as described herein.

Various aspects of the invention will now be illustrated in non-limiting ways by reference to the following examples.

EXAMPLES

Example 1

Materials and Methods

Endophyte Strains
Endophyte strains used in this study are listed in Table 1 below:

TABLE 1

| Strain | Origin | Reference |
| --- | --- | --- |
| AR3002 | China | Card et al., 2014 |
| AR3060 | China | Card et al., 2014 |
| AR3067 | Kazakhstan | Card et al., 2014 |
| AR3070 | Mongolia | Card et al., 2014 |
| AR3108 | Canada | Unpublished |
| AR3013 | Iran | Unpublished |

Naturally occurring endophyte strains were isolated from parent plants as previously described (Simpson et al., 2012). Fungal cultures were grown on potato dextrose agar as described previously (Fleetwood et al., 2007).

Inoculation of Wheat Alien Chromosome Substitution and Addition Lines

Four independent experiments involving inoculation of wheat lines sourced from the Arid Land Research Center (ALRC) (Tottori University, Tottori, Japan) were performed as described below.

In experiment 1 (Tottori, Japan, March 2015), five seed of each of 156 lines consisting of wheat with various alien chromosome introductions from species of *Aegilops, Agropyron, Elymus, Hordeum, Leymus, Psathyrostachys, Haynaldia* and *Secale* and the cultivar 'Chinese Spring' (Table 4) were inoculated, as described by Latch & Christensen (1985), using strain AR3060 which had previously been demonstrated to infect the wheat cultivar "Monad", albeit with a compromised host phenotype (Simpson et al., 2014). Eleven of these lines and 'Chinese Spring' were additionally inoculated with strains AR3002 and AR3067. Plants were grown for ca. 6 weeks in 2 cm cell flats containing commercial potting mix before identifying infected individuals by tissue-print immunoblotting as previously described (Simpson et al., 2012). Plants that were demonstrated to be infected with *Epichloë* by immunoblot were grown for a further 3 months in the same cell flats under glasshouse conditions to complete their full life cycle.

In experiment 2 (Tottori, Japan, March 2016), a number of TACBOW lines that became infected in experiment 1 were re-inoculated (40 seedlings of each line) with strain AR3060 as described above. In addition, inoculations into the wheat cultivars "Monad" and "Chinese Spring" were performed as controls, since neither of these cultivars contain alien chromosome introgressions and "Chinese Spring" was used to generate the majority of TACBOW lines (Table 4). Plants that were demonstrated to be infected with *Epichloë* by immunoblot were transplanted into 10×30 cm deep pots containing commercial potting mix and grown for a further 3 months under glasshouse conditions to complete their full life cycle. Endophyte-free plants of the same lines were also transplanted under equivalent conditions to serve as direct comparisons to the infected plants.

In experiment 3 (Palmerston North, New Zealand, September 2016), TACBOW0011, previously shown to transmit AR3060 to grain in Japan, was inoculated with AR3070 (Table 4). Due to the death of control inoculations into "Chinese Spring" in experiment 2, further inoculations with strain AR3060, in addition to AR3070, were performed into this background cultivar which, as described above, was used to generate the majority of TACBOW lines, but contains no alien chromosome introgressions (Table 4).

In experiment 4 (Palmerston North, New Zealand, October 2018) TACBOW0011 was inoculated with a single strain of either AR3002, AR3060, AR3070, AR3108, AR3067 or AR3013 as described above. Seed of TACBOW0018, TACBOW0044, TACBOW0067 and TACBOW0237 infected with AR3060 was obtained from Tottori, Japan and grown in Palmerston North, New Zealand. Eighteen different TACBOW lines were inoculated with AR3002 as described above. Infection for all plants was confirmed by immunoblotting and chemistry methods as described above.

Phenotyping

Plants were phenotyped at the completion of their life cycle. Plants that were originally infected as determined by earlier immunoblotting results, were confirmed as still being *Epichloë* infected by microscopy and/or fungal isolation as described below. Infected individuals were compared to plants of the same line that did not become infected.

Epidermal Leaf Peel

Tillers were selected from mature plants for endophyte detection. Clean, live sheath tissue was placed under a dissecting microscope at 16× magnification with the adaxial epidermis facing up. A shallow transverse cut was made with a scalpel and the epidermis gently lifted, separated and pulled off the sheath. Tissue was mounted in a drop of aniline blue dye (glycerol 50%, lactic acid 25%, water 24.95%, aniline blue 0.05%) and heated over a naked flame and examined at 100× and 400× using a compound microscope.

Seed Squash

Grain were covered with a 5% sodium hydroxide solution and left to imbibe overnight. The following day the solution was decanted, and the samples thoroughly rinsed with tap water. Samples were covered with Garner's solution (0.325 g aniline blue, 100 ml water and 50 mL 85% lactic acid) and heated to boiling on a hot plate. After cooling, the palea and lemma were removed and the softened grain mounted on a microscope slide, a cover slip placed over the mounted grain and gentle, even pressure applied squashing the preparation. The preparations were then examined under a compound light microscope at 100× and 400× magnification.

Fungal Isolation

Fungus was isolated from plants following surface sterilisation of plant tissue as described by Christensen et al. (2002). Blade tissue was surface sterilised by quick rinse with 96% ethanol and a 1-minute soak in a sodium hypochlorite solution (10% Janola: 42 g/L NaOCl domestic bleach), followed by rinsing twice in sterile water. Tissue was plated on to antibiotic potato dextrose agar. Plates were incubated at 22-25° C. for 3-5 days.

Results and Discussion

*Epichloë* Infection of Wheat Alien Chromosome Addition Substitution Lines.

Experiment 1

Of the 156 lines inoculated in experiment 1, immunoblot results indicated that 98 lines appeared to be infected (Table 4) with *Epichloë* with the remaining lines being uninfected. All lines were subsequently phenotyped at maturity. Un-infected lines were universally tall and floral with fully developed grain. Of the infected lines, three classes of material were identified (Table 4). These included tall floral plants with fully developed grain that were comparable to un-infected plants of the same line (class 1), tall floral plants delayed in their maturation which was exemplified by a 'stay green' phenotype and a protracted elaboration and maturation of floral spike (class 2), and abnormal phenotype plants that were short in stature and failed to produce inflorescences (class 3). Additional evidence for endophyte infection was obtained for a sub-set of plants from each of the three infection phenotypes using a combination of fungal isolation and microscopy of leaf and seed material. Although not all of the plants that had a delayed maturation were confirmed as infected in this way this phenotype is indicative of endophyte infection and were classified as such for further analysis. For class 1 plants, unless confirmed to be infected by isolation or microscopy, loss of endophyte from tillers of these plants cannot be ruled out.

Experiment 2

Of the 8 TACBOW lines and 2 control lines inoculated in experiment 2 (Table 4) most plants did not survive to maturity. Of those that did, two lines (TACBOW0059 and TACBOW0236) were confirmed as infected and displayed a tall floral class 1 phenotype that was comparable to uninfected plants of the same line (FIG. 1b-1c). Whilst no infected "Chinese Spring" plants survived, uninfected plants were tall and floral (FIG. 1a) and served as an additional control to compare infected TACBOW lines. Several "Monad" plants were confirmed as infected and these displayed (FIG. 1d) a dwarf host phenotype similar to that reported in Simpson et al. (2014).

Experiment 3

The results obtained with TACBOW0011 in experiment 1 indicated that this line was particularly good at hosting *Epichloë* strain AR3060, with all plants examined producing fully mature infected grain (Table 4). In experiment 3 we inoculated this line with AR3060 and an additional strain, AR3070. These two strains were also inoculated into the background "Chinese Spring" cultivar in which no alien chromosome additions exist. We obtained infection of TACBOW0011 with AR3060, as expected, but we also obtained infected plants with AR3070. AR3060 infected plants displayed a tall floral class 1 infection phenotype (Table 4). However, whereas AR3060 infected plants produced mature infected seed that could transmit endophyte to the next generation, plants infected with AR3070 failed under the conditions employed to set fertile seed and were therefore a class 2 phenotype.

The inoculation of "Chinese Spring" in this experiment did produce some infected individuals. However, in all cases they displayed a class 3 infection phenotype in which the plants were short and non-floral.

Experiment 4

The phenotype class for each of the infected lines for experiment 4 is shown in Table 5. All the TACBOW lines infected with the strain AR3060 displayed a tall floral class 1 phenotype. Most TACBOW lines exhibited a delay in growth when infected with strains AR3013, AR3067, AR3070 or AR3108, meaning a full growth cycle was not completed before the conclusion of experiment 5. TACBOW0011 displayed a class 1 tall floral infection phenotype when infected with AR3002, AR3060, AR3070 or AR3108. TACBOW0011 infected with AR3070 displayed a class 2 infection phenotype.

A summary of successful inoculations is included in Table 6 for those endophyte strains where at least some of the inoculated plants were of substantially normal phenotype and were able to progress through a normal life cycle. Seeds were collected from the plants as indicated in Table 6.

Conclusion

The inoculation of commercial hexaploid wheat with *Epichloë* has to date been unsuccessful with resulting infected plants having compromised phenotypes. This result was confirmed here with inoculations of the wheat cultivar Chinese Spring (no chromosome additions or substitutions) based on challenge with several *Epichloë* strains. However, in this study, inoculation of Chinese Spring based wheat containing alien chromosome additions or substitutions sourced from rye and wild grass species (many of which also host *Epichloë*) resulted in the production of infected tall floral plants.

Example 2

Detection of Genetic Variation of Fungal Endophyte Strains

Endophyte strains AR3002, AR3013, AR3060, AR3067, AR3070 and AR3108 were characterised and distinguished for genetic variation by DNA 'fingerprinting' based on genotypic data derived from up to 22 selected simple sequence repeat (SSR) marker loci using primer sequences of Table 2. These primer sequences had previously been shown to generally amplify *Epichloë* endophyte polymorphic DNA sequences from when the endophytes are in planta (Moon et al. 1999; Kirkby et al, 2011; Simpson et al. 2012; Card et al, 2014).

Samples of about 100 mg fresh weight of basal tiller were used to extract total genomic DNA (plant+endophyte), following the plant DNA isolation procedure of the FastDNA kit as recommended by the manufacturer (MP Biomedicals, Solon, Ohio, USA) for plant samples.

SSR amplification was conducted with oligonucleotide primer pairs, using one of two polymerase chain reaction (PCR) protocols (Table 2). In both protocols PCR was carried out using an iCycler thermocycler (BioRad, Hercules, California, USA).

Protocol 1 was as described by Moon (Moon et al., 1999), except that an annealing temperature of 60° C. was used. In this protocol forward primers were labelled at the 5' terminus with the fluorophore 6-FAM™ (Applied Biosystems, Foster City, California, USA).

In Protocol 2 forward primers were synthesised with a 21 nucleotide M13 tail sequence at the 5'-terminus (5'-TGTAAAACGACGGCCAGT-3') (SEQ ID NO: 1), to facilitate universal labelling of PCR products by a 6-FAM™-labelled M13 primer (Schuelke, 2000). Reverse primers were synthesised with the sequence 5'-GTTTCTT-3" (SEQ ID NO: 2) at the 5'-terminus ends to promote non-templated adenylation at the 3'-terminus end of PCR product (Brownstein et al., 1996). A 10 µL PCR reaction volume was used, containing approximately 10 ng of total genomic DNA, 2.5 mM magnesium chloride, 1×PCR buffer, 0.05 mM of each dNTP, 0.0375 µM forward primer, 0.15 µM reverse primer, 0.15 µM of fluorescent-labelled M13 primer and 0.75 U of Platinum Taq DNA polymerase (Invitrogen, Carlsbad, California). PCR was carried out using the following profile: (1) 94° C. for 4:00 minutes, (2) 30 cycles of: 94° C. for 30 seconds, 55° C. for 30 seconds and 72° C. for 30 seconds, (3) 8 cycles of: 94° C. for 30 seconds, 53° C. for 30 seconds and 72° C. for 30 seconds, (4) 72° C. for 30 minutes (after Schuelke 2000).

PCR products were analysed by capillary electrophoresis on an ABI 3130xl Genetic Analyser using a 22 cm capillary array with POP-7™ polymer (Applied Biosystems). GS500 LIZ (Applied Biosystems) was used as an internal size standard. Electropherograms were analysed using ABI Prism GeneScan (v 3.7, Applied Biosystems), and genotype data was scored using Genemarker analysis software (Soft-Genetics LLC, Pennsylvania, USA).

The inventors note here that in their experience, allele sizes will vary in some analyses according to a number of factors. For example, estimates of fragment (allele) sizes based on capillary electrophoresis are affected by factors including, but not limited to, the type of instrument, the length of the capillary array, the type of polymer used and environmental variables including ambient temperature. Accordingly, the SSR allele sizes in bp that are reported herein, including those in Table 3 below, are associated with the analysis platform described and also include a confidence interval of ±0.8 bp.

Plants examined above were then further characterised by performing chemical analyses. Six infected seedlings were further examined for the presence of alkaloids, attributable to the presence of endophytes, such as indole diterpenes, ergot alkaloids, peramine and lolines.

TABLE 2

SSR primer sequences.

| SSR | | Primer sequences (5'-3') | PCR protocol | SEQ ID NO: |
|---|---|---|---|---|
| B10 | forward | CGCTCAGGGCTACATACACCATGG | 1 | 3 |
| | reverse | CTCATCGAGTAACGCAGGCGACG | | 4 |
| B11 | forward | CATGGATGGACAAGAGATTGCACG | 1 | 5 |
| | reverse | TTCACTGCTACAATTCTGTCCAGC | | 6 |
| ans016 | forward | CACAAAGACAAACGCCAAAAG | 2 | 7 |
| | reverse | GCAAAGCTCACAGACAAAGGTC | | 8 |
| ans019 | forward | TACCTCTGCACGGTGTATTCC | 2 | 9 |
| | reverse | TGCATAACACTCACCTTATAGTCG | | 10 |
| ans033 | forward | GCGTTGAGGAGGCTAGATAGAA | 2 | 11 |
| | reverse | TTCCAAGCTGAACAAAAGTCAA | | 12 |
| ans036 | forward | ATTTGCAGCAGAGATGATGTGT | 2 | 13 |
| | reverse | CCTGCACCGGACTGTTAGTAAT | | 14 |
| egs027 | forward | GATGACGTATCTTGATGCTACCAC | 2 | 15 |
| | reverse | CGTGTATAAAGTTCGGGATCCTAT | | 16 |
| egs031 | forward | GAGATATCCCGTCTCCTGATCTAA | 2 | 17 |
| | reverse | CACAGCGTTACACTATCAACTTCC | | 18 |
| ces0004 | forward | CACTAAACACACCCAAGAACAAGA | 2 | 19 |
| | reverse | AGACAGGTAAGAAGTTTTCCCCTT | | 20 |
| ces0022 | forward | AGCTTTCCAATGACGACATACATA | 2 | 21 |
| | reverse | TAATTTAGGGTAGCATTTTCTCCG | | 22 |
| ces0041 | forward | GGTCCCTATTCTAATGCAGGTATG | 2 | 23 |
| | reverse | CAGTGTACGGGACTTTGTCAATAC | | 24 |
| ces0054 | forward | TGTATAATAAACATGGCGTGCTCT | 2 | 25 |
| | reverse | GTGTTGAAAGTTGTTGGATCACTC | | 26 |
| ces0060 | forward | CGAAATTGTAGACTATGTTGGAGC | 2 | 27 |
| | reverse | GTAGATGTATTTTGAGCAGGGCTT | | 28 |
| ces0061 | forward | GAGTGAGACCCGGTGTAGTAAGTC | 2 | 29 |
| | reverse | GAGTCATTCTTCGTCCATTGTCTT | | 30 |
| ces0067 | forward | GAAATGAGGCGTCTATCTTAAAGC | 2 | 31 |
| | reverse | TTTCTTGATTTCCAAAGAACAACA | | 32 |

TABLE 2-continued

SSR primer sequences.

| SSR | | Primer sequences (5'-3') | PCR protocol | SEQ ID NO: |
|---|---|---|---|---|
| ces0075 | forward | CAGTCATCGATTAAAAGTGAGCAT | 2 | 33 |
| | reverse | ATGTCATCTGCTTCAACAAGAGTC | | 34 |
| ces0076 | forward | TCTTCCATACAATTTCTTCCCTTC | 2 | 35 |
| | reverse | ACTAGTCAATAGCACAAATTGCCA | | 36 |
| ces0078 | forward | AGCCCTAGCCTATACATCTTTCCT | 2 | 37 |
| | reverse | AATGGGCTTTTCCATTCAATAATA | | 38 |
| ces0089 | forward | AAATGATTGTTCGCTGTATGCTAA | 2 | 39 |
| | reverse | ATGTCATGTTTGATTCCATTTTTG | | 40 |
| ces0093 | forward | CTGCTAGACATACTTGGAACATGG | 2 | 41 |
| | reverse | CAGTCGAATAATTTAGGGAGCATT | | 42 |
| ces0094 | forward | ACTGAGTGATGGTAGAAAAGAGGG | 2 | 43 |
| | reverse | CAGAATTTCTCCCATATATACGCC | | 44 |
| ces0095 | forward | TCATCTCTTCAAGACTTTCCTCCT | 2 | 45 |
| | reverse | TTTAGTGTCACTTCTTCATCTCGC | | 46 |

TABLE 3

SSR allele sizes for strains AR3002, AR3013, AR3060, AR3067, AR3070 and AR3108 in base pairs (bp) ± 0.8.

| | Allele size (bp) | | | | | |
|---|---|---|---|---|---|---|
| SSR | AR3002 | AR3060 | AR3067 | AR3070 | AR3108 | AR3013 |
| B10 | 188 | 185 | 159, 185 | 172 | 181, 193 | 177, 185 |
| B11 | 112 | 112 | 112, 148 | 116 | 127, 138 | 112 |
| ans016 | 282 | 282 | 282, 309 | 282 | 282, 294 | 282, 291 |
| ans019 | 204 | 204 | 204 | 204 | 197 | 194 |
| ans033 | 181 | 176 | 176 | 176 | 184, 194 | 181 |
| ans036 | 286 | 286 | 267, 286 | 272 | 259, 270 | 286 |
| egs027 | 359 | 359 | 345, 359 | 366 | 347, 351 | 349, 359 |
| egs031 | 259 | 259 | 259, 283 | 283 | 308 | 259, 277 |
| ces0004 | 185 | 189 | 185 | 174 | 179, 187 | 189 |
| ces0022 | 209 | 209 | 204, 209 | 208 | 206, 208 | 209, 215 |
| ces0041 | 261 | 259 | 247, 257 | 251 | 254, 286 | 254, 261 |
| ces0054 | 261 | 261 | 261 | 267 | 258, 283 | 261, 298 |
| ces0060 | 238 | 238 | 238, 250 | 240 | 246, 257 | 238, 250 |
| ces0061 | 162 | null* | 154, 177 | 166 | 221, 252 | 149, 171 |
| ces0067 | 277 | 277 | 277, 281 | 268 | 272, 296 | 277 |
| ces0075 | 243 | 243 | 243, 278 | 226 | 249, 263 | 243 |
| ces0076 | 157 | 180 | 180 | 196 | 153, 236 | 153 |
| ces0078 | 310 | 303 | 294, 303 | 303 | 292, 298 | 294, 303 |
| ces0089 | 165 | 165 | 165 | 159 | 154, 165 | 162, 165 |
| ces0093 | 145 | 145 | 143, 145 | 144 | 143, 145 | 145, 153 |
| ces0094 | 329 | 327 | 313, 327 | 323 | 313, 318 | 315, 329 |
| ces0095 | 360 | 360 | 360 | 355 | 334 | 360 |

*SSR primer pair produces no amplicon

TABLE 4

Infection phenotype class of combinations of TACBOW wheat lines and selected Epichloe strains from experiments 1 to 3

| Line | Experiment | Infection Phenotype class* (AR3060 unless otherwise specified) |
|---|---|---|
| Chinese Spring | 1,2,3 | 3, 3(AR3070) |
| Monad | 2 | 3 |
| TACBOW0001 | 1 | 3 |
| TACBOW0003 | 1 | 1 |
| TACBOW0004 | 1 | #N/A |
| TACBOW0005 | 1, 2 | 1* |
| TACBOW0006 | 1 | #N/A |
| TACBOW0007 | 1,2 | 2* |
| TACBOW0008 | 1 | 2* |
| TACBOW0009 | 1 | 2* |
| TACBOW0010 | 1,2 | 1 |
| TACBOW0011 | 1,2,3 | 1*, 1* (AR3070), 1* (AR3002), 1 (AR3108) |
| TACBOW0012 | 1,2 | 3 |
| TACBOW0013 | 1 | #N/A |
| TACBOW0014 | 1 | #N/A |
| TACBOW0015 | 1 | 3 |
| TACBOW0016 | 1 | 3 |
| TACBOW0017 | 1 | 3 |
| TACBOW0018 | 1 | 1 |
| TACBOW0020 | 1 | 2,3 (AR3002), 3 (AR3067) |
| TACBOW0024 | 1 | 2, 3 (AR3002), 3 (AR3067) |
| TACBOW0025 | 1 | 2 |
| TACBOW0026 | 1 | 3 |
| TACBOW0027 | 1 | #N/A |
| TACBOW0028 | 1 | 1, 3 (AR3002) |
| TACBOW0029 | 1 | #N/A |
| TACBOW0032 | 1 | 3 |
| TACBOW0034 | 1 | 3 |
| TACBOW0035 | 1 | #N/A |
| TACBOW0036 | 1 | 3 |
| TACBOW0038 | 1 | 2 |
| TACBOW0039 | 1 | #N/A |
| TACBOW0040 | 1 | 3 |
| TACBOW0041 | 1 | 3 |
| TACBOW0042 | 1 | #N/A |
| TACBOW0043 | 1 | 3 |
| TACBOW0044 | 1 | #N/A |
| TACBOW0045 | 1 | 1 |
| TACBOW0046 | 1 | 3 |
| TACBOW0047 | 1 | 3 |
| TACBOW0048 | 1 | 3 |
| TACBOW0049 | 1 | 3 |
| TACBOW0051 | 1 | #N/A |
| TACBOW0052 | 1 | 2 |
| TACBOW0053 | 1 | 2 |
| TACBOW0054 | 1 | 1 |
| TACBOW0055 | 1 | 3 |
| TACBOW0056 | 1 | 2 |
| TACBOW0057 | 1 | 3 |

TABLE 4-continued

Infection phenotype class of combinations of TACBOW wheat lines and selected Epichloe strains from experiments 1 to 3

| Line | Experiment | Infection Phenotype class* (AR3060 unless otherwise specified) |
|---|---|---|
| TACBOW0059 | 1,2 | 1 * |
| TACBOW0060 | 1 | #N/A |
| TACBOW0061 | 1 | #N/A |
| TACBOW0062 | 1 | #N/A |
| TACBOW0064 | 1 | 2*, 3 (AR3002) |
| TACBOW0065 | 1 | #N/A |
| TACBOW0066 | 1 | 3 (AR3002), 3* (AR3067) |
| TACBOW0067 | 1 | 2, 2 (AR3002), 2 (AR3067) |
| TACBOW0068 | 1 | #N/A |
| TACBOW0069 | 1 | #N/A |
| TACBOW0070 | 1 | #N/A |
| TACBOW0123 | 1 | #N/A |
| TACBOW0124 | 1 | 2 |
| TACBOW0125 | 1 | 3 |
| TACBOW0126 | 1 | 3 |
| TACBOW0127 | 1 | #N/A |
| TACBOW0128 | 1 | 1 |
| TACBOW0133 | 1 | #N/A |
| TACBOW0136 | 1 | #N/A |
| TACBOW0137 | 1 | #N/A |
| TACBOW0138 | 1 | 3 |
| TACBOW0189 | 1 | 3 |
| TACBOW0190 | 1 | 3 |
| TACBOW0191 | 1 | #N/A |
| TACBOW0193 | 1 | 3 |
| TACBOW0195 | 1 | 3 |
| TACBOW0196 | 1 | 2 |
| TACBOW0197 | 1 | 2 |
| TACBOW0198 | 1 | 2 |
| TACBOW0201 | 1 | #N/A |
| TACBOW0202 | 1 | #N/A |
| TACBOW0204 | 1,2 | 2 |
| TACBOW0205 | 1 | #N/A |
| TACBOW0206 | 1 | 3 |
| TACBOW0208 | 1 | #N/A |
| TACBOW0209 | 1 | 1 |
| TACBOW0213 | 1 | #N/A |
| TACBOW0214 | 1 | 3 |
| TACBOW0215 | 1 | 2 |
| TACBOW0217 | 1 | 3 |
| TACBOW0219 | 1 | 3 |
| TACBOW0220 | 1 | 3 |
| TACBOW0221 | 1 | 1 |
| TACBOW0222 | 1 | 3 |
| TACBOW0224 | 1 | 2* |
| TACBOW0225 | 1 | #N/A |
| TACBOW0226 | 1 | 1 |
| TACBOW0227 | 1 | #N/A |
| TACBOW0228 | 1 | #N/A |
| TACBOW0229 | 1 | #N/A |
| TACBOW0230 | 1 | 3 |
| TACBOW0231 | 1 | #N/A |
| TACBOW0232 | 1 | 2* |
| TACBOW0233 | 1 | #N/A |
| TACBOW0235 | 1 | 3 |
| TACBOW0236 | 1,2 | 1 * |
| TACBOW0237 | 1 | #N/A |
| TACBOW0239 | 1 | 3 |
| TACBOW0240 | 1 | #N/A |
| TACBOW0242 | 1 | #N/A |
| TACBOW0244 | 1 | 1 |
| TACBOW0245 | 1 | 3 |
| TACBOW0246 | 1 | 3 |
| TACBOW0247 | 1 | #N/A |
| TACBOW0249 | 1 | #N/A |
| TACBOW0250 | 1 | 2 |
| TACBOW0252 | 1 | 3 |
| TACBOW0253 | 1 | #N/A |
| TACBOW0254 | 1 | 3 |
| TACBOW0256 | 1 | 2 |
| TACBOW0257 | 1 | #N/A |
| TACBOW0258 | 1 | #N/A |
| TACBOW0259 | 1 | 3 |
| TACBOW0260 | 1 | 1 |
| TACBOW0261 | 1 | 1 |
| TACBOW0262 | 1 | 3 |
| TACBOW0264 | 1 | #N/A |
| TACBOW0265 | 1 | 3 |
| TACBOW0266 | 1 | #N/A |
| TACBOW0267 | 1 | 2 |
| TACBOW0268 | 1 | #N/A |
| TACBOW0270 | 1 | #N/A |
| TACBOW0271 | 1 | #N/A |
| TACBOW0272 | 1 | 1 |
| TACBOW0273 | 1 | 2 |
| TACBOW0274 | 1 | #N/A |
| TACBOW0275 | 1 | 1 |
| TACBOW0276 | 1 | #N/A |
| TACBOW0277 | 1 | #N/A |
| TACBOW0278 | 1 | 2 |
| TACBOW0279 | 1 | 2 |
| TACBOW0280 | 1 | 3 |
| TACBOW0281 | 1 | #N/A |
| TACBOW0282 | 1 | 2 |
| TACBOW0283 | 1 | 3 |
| TACBOW0284 | 1 | #N/A |
| TACBOW0286 | 1 | #N/A |
| TACBOW0287 | 1 | #N/A |
| TACBOW0288 | 1 | 2 |
| TACBOW0290 | 1 | 2 |
| TACBOW0291 | 1 | 3 |
| TACBOW0292 | 1 | #N/A |
| TACBOW0293 | 1 | 3 |
| TACBOW0295 | 1 | 2 |
| TACBOW0296 | 1 | #N/A |
| TACBOW0297 | 1 | #N/A |
| TACBOW0298 | 1 | #N/A |
| TACBOW0299 | 1 | 3 |

\* = class 1 and 2 plants that were confirmed infected.
N/A = Not applicable: these plants were either not infected, or they died.

TABLE 5

Infection phenotype class of combinations of TACBOW wheat lines and selected Epichloë strains from experiment 4

| | Infection Phenotype Class | | | | | |
|---|---|---|---|---|---|---|
| Line | AR3002 | AR3013 | AR3060 | AR3067 | AR3070 | AR3108 |
| TACBOW0003 | 3 | #N/A | #N/A | #N/A | #N/A | #N/A |
| TACBOW0005 | #N/A | #N/A | #N/A | #N/A | #N/A | #N/A |
| TACBOW0010 | 3 | #N/A | #N/A | #N/A | #N/A | #N/A |
| TACBOW0011 | 1 | 3 | 1 | #N/A | 1 | 1 |
| TACBOW0018 | #N/A | #N/A | 2 | #N/A | # N/A | #N/A |
| TACBOW0028 | #N/A | #N/A | #N/A | #N/A | #N/A | #N/A |
| TACBOW0044 | #N/A | #N/A | 1 | #N/A | #N/A | #N/A |
| TACBOW0045 | 3 | #N/A | #N/A | #N/A | #N/A | #N/A |
| TACBOW0054 | 3 | #N/A | #N/A | #N/A | #N/A | #N/A |
| TACBOW0059 | 3 | #N/A | #N/A | #N/A | #N/A | #N/A |
| TACBOW0128 | #N/A | #N/A | #N/A | #N/A | #N/A | #N/A |
| TACBOW0209 | #N/A | #N/A | #N/A | #N/A | #N/A | #N/A |
| TACBOW0221 | #N/A | #N/A | #N/A | #N/A | #N/A | #N/A |
| TACBOW0226 | #N/A | #N/A | #N/A | #N/A | #N/A | #N/A |
| TACBOW0236 | #N/A | #N/A | #N/A | #N/A | #N/A | #N/A |
| TACBOW0237 | #N/A | #N/A | 1 | #N/A | #N/A | #N/A |
| TACBOW0244 | 3 | #N/A | #N/A | #N/A | #N/A | #N/A |
| TACBOW0260 | 3 | #N/A | #N/A | #N/A | #N/A | #N/A |
| TACBOW0261 | 3 | #N/A | #N/A | #N/A | #N/A | #N/A |
| TACBOW0272 | 3 | #N/A | #N/A | #N/A | #N/A | #N/A |
| TACBOW0275 | #N/A | #N/A | #N/A | #N/A | #N/A | #N/A |

N/A = Slow growing plants—data not available at time of filing.

TABLE 6

Strains inoculated into and infecting TACBOW lines and examples of seed production in TACBOW lines.

| Endophyte | TACBOW Line | Inoculation of TACBOW line attempted | Infected plants of TACBOW line obtained | Infected plants of TACBOW line produced seed | Seed of TACBOW line was infected with endophyte | Seed was infected with viable endophyte |
|---|---|---|---|---|---|---|
| AR3002 | TACBOW0003 | YES | YES | N/A | N/A | N/A |
|  | TACBOW0005 | YES | NO | N/A | N/A | N/A |
|  | TACBOW0010 | YES | YES | N/A | N/A | N/A |
|  | TACBOW0011 | YES | YES | YES | YES | YES |
|  | TACBOW0018 | YES | YES | YES | YES | YES |
|  | TACBOW0028 | YES | NO | N/A | N/A | N/A |
|  | TACBOW0045 | YES | YES | N/A | N/A | N/A |
|  | TACBOW0054 | YES | YES | N/A | N/A | N/A |
|  | TACBOW0059 | YES | YES | N/A | N/A | N/A |
|  | TACBOW0128 | YES | NO | N/A | N/A | N/A |
|  | TACBOW0209 | YES | NO | N/A | N/A | N/A |
|  | TACBOW0221 | YES | NO | N/A | N/A | N/A |
|  | TACBOW0226 | YES | NO | N/A | N/A | N/A |
|  | TACBOW0236 | YES | NO | N/A | N/A | N/A |
|  | TACBOW0244 | YES | YES | N/A | N/A | N/A |
|  | TACBOW0260 | YES | YES | N/A | N/A | N/A |
|  | TACBOW0261 | YES | YES | N/A | N/A | N/A |
|  | TACBOW0272 | YES | YES | N/A | N/A | N/A |
|  | TACBOW0275 | YES | YES | N/A | N/A | N/A |
| AR3013 | TACBOW0011 | YES | YES | YES | NO | NO |
| AR3060 | TACBOW0011 | YES | YES | YES | YES | YES |
|  | TACBOW0018 | YES | YES | YES | YES | YES |
|  | TACBOW0044 | YES | YES | YES | YES | YES |
|  | TACBOW0067 | YES | YES | YES | YES | YES |
|  | TACBOW237 | YES | YES | YES | YES | YES |
| AR3070 | TACBOW0011 | YES | YES | NO | NO | NO |
| AR3108 | TACBOW0011 | YES | YES | NO | NO | NO |

N/A—Slow growing plants—data not available at time of filing.

Example 3

Alkaloid Production in Endophyte Infected TACBOW Plants

Methods

Extraction and Detection of Peramine/Cyclo[Pro,Arg], Ergot Alkaloids, and Lolines.

Material for analysis was freeze-dried and ground prior to chemical analysis (Table 9). Sub-samples of freeze-dried and ground material were extracted with 80% (v/v) methanol containing internal standards (1.7 μg/mL homoperamine nitrate (BDG Synthesis, New Zealand), 0.51 μg/mL ergotamine (Sigma), 0.10 μg/mL festuclavine (ALFARMA s.r.o., Czech Republic)), with the sub-sample weight determining the volume of extraction solvent used (1 mL for 30-60 mg, 500 μL for 30-15 mg, 250 μL for <15 mg). Samples were extracted by end-over-end rotation (30 rpm) for 60 minutes in the dark prior to being centrifuged at 4500×g for 5 minutes, and the supernatant transferred via syringe filter (13 mm diameter, 0.45-μm-pore polytetrafluoroethylene syringe filter (Jet BioFil, Guangzhou, China)) into an amber 12×32 mm HPLC vial. Samples were analysed using an LTQxl™ linear ion-trap mass spectrometer (Thermo Scientific, USA). Each sample (1 μL injection) was chromatographically separated on a Poroshell HILIC-Z 150×2.1 mm (2.7 μm) column (Agilent Technologies, USA) using a linear gradient profile (eluent A is aqueous 16 mM ammonium formate and eluent B is 97% acetonitrile with 0.1% formic acid) with time 0 min ($T_0$) at 92.8% B, $T_{3.5}$ at 83% B, $T_5$ at 83% B, and $T_{5.5}$ at 92.8% B, followed by equilibration to initial conditions over the following 2 minutes. MRMs as described in Table 7 were used to quantify and confirm the identity of the analytes and internal standards.

TABLE 7

Retention times and MRM transitions for analytes and internal standards. Internal standards (marked ") were used for preceding analytes.

| Compound | Retention time | Product ion | Quantitative ion | Confirmation ion |
|---|---|---|---|---|
| Peramine | 2.85 min | 248 m/z | 206 m/z | 231 m/z |
| Cyclo[Pro,Arg] | 4.10 min | 254 m/z | 195 m/z | 194 m/z |
| N-Acetyl Norloline | 3.20 min | 183 m/z | 165 m/z | 140 m/z |
| N-Formyl Loline | 2.95 min | 183 m/z | 155 m/z | 124 m/z |
| N-Acetyl Loline | 2.65 min | 197 m/z | 155 m/z | 154 m/z |
| Homoperamine* | 2.60 min | 262 m/z | 245 m/z | 220 m/z |
| Chanoclavine | 2.05 min | 257 m/z | 226 m/z | 208 m/z |
| Festuclavine* | 1.47 min | 241 m/z | 210 m/z | 168 m/z |
| Ergovaline | 1.80 min | 534 m/z | 286 m/z | 516 m/z |
| Ergotamine* | 1.65 min | 582 m/z | 268 m/z | 564 m/z |
| Ergovalinine | 1.35 min | 534 m/z | 516 m/z | — |
| Ergotaminine* | 1.20 min | 582 m/z | 564 m/z | — |

Extraction and Detection of Dahurelmusin A, And Indole Diterpenes.

Material for analysis was freeze-dried and ground prior to chemical analysis (Table 9). Sub-samples of freeze-dried and ground material were extracted with 80% (v/v) methanol with the sub-sample weight determining the volume of extraction solvent used (1 mL for 30-60 mg, 500 μL for 30-15 mg, 250 μL for <15 mg). Samples were extracted by end-over-end rotation (30 rpm) for 60 minutes in the dark prior to being centrifuged at 4500×g for 5 minutes, and the supernatant transferred via syringe filter (13 mm diameter, 0.45-μm-pore polytetrafluoroethylene syringe filter (Jet Bio-Fil, Guangzhou, China)) into an amber 12×32 mm HPLC vial. Samples were analysed using an LTQxl™ linear ion-trap mass spectrometer (Thermo Scientific, USA). Each sample (1 μL injection) was chromatographically separated on a Accucore C18 150×2.1 mm (2.6 μm) column (Thermo Scientific, USA) using a linear gradient profile (eluent A is aqueous 0.1% formic acid and eluent B is 97% acetonitrile with 0.1% formic acid) with time 0 min ($T_0$) at 2% B, $T_{17}$ at 100% B, $T_{19}$ at 100% B, and $T_{20}$ at 2% B, followed by equilibration to initial conditions over the following 5 minutes. MRMs as described in Table 8 were used to quantify and confirm the identity of the analytes and internal standards.

TABLE 8

Retention times and MRM transitions for analytes and internal standards.

| Compound | Retention time | Product ion | Quantitative ion | Confirmation ion |
|---|---|---|---|---|
| Dahurelmusin A | 6.65 min | 355 m/z | 266 m/z | 284 m/z |
| Paspaline | 15.25 min | 422 m/z | 130 m/z | 407 m/z |
| Terpendole E | 11.55 min | 438 m/z | 130 m/z | 423 m/z |
| Paxitriol | 11.00 min | 438 m/z | 130 m/z | 423 m/z |
| Paxilline | 11.40 min | 436 m/z | 130 m/z | 423 m/z |

Quantitation of paxillin was achieve through the use of an external standard, while semi-quantitation of the remaining indole diterpenes was achieved through reference to paxillin. Therefore, paxillin is reported in μg/g, while the other indole diterpenes detected are reported as paxillin equivalent units (response factor for all other indole diterpenes is calculated as being the same as paxillin). No standards (or similar compounds suitable as standards) were available for Dahurelmusin A, therefore Dahurelmusin A is reported as area under the curve.

Example 4

TACBOW/Endophyte Combinations Having Bioactivity Against Argentine Stem Weevil

Methods: A randomised block design with ten replicates, three treatments and one Nil endophyte control was used. The three treatments were, TACBOW0011 plants inoculated with endophyte AR3002, TACBOW0011 plants inoculated with endophyte AR3060 and TACBOW0011 plants inoculated with endophyte AR3070. The control consisted of endophyte free TACBOW0011 plants. Endophyte presence for the treatment plants was assessed using a standard tissue-print immunoblot technique. One tiller per plant was tested. The experiment was set-up in a 20° C. controlled environment room with 12:12 light:dark regime on 19 Dec. 2018. Adult Argentine stem weevils (*Listronotus bonariensis*) were collected in the field using an insect suction sampler. Six adult Argentine stem weevils were added to each of the plants and a net cage was put over each plant.

On 27th December the light regime was changed to 14:10 light:dark. On 9 Jan. 2019, covers were removed and the number of tillers on each plant was recorded. The number of adult feeding scars on each leaf was counted taking into account the size of the scar. The number of weevil eggs on each tiller was also recorded.

Two weeks later (24-25 Jan. 2019) each tiller was examined and larval damage was scored on a scale of 0-3; where 0=no damage, 1=larval feeding on external surface of tiller only, 2=larva has penetrated and partially mined the tiller and 3=larva has penetrated and extensively mined the tiller

TABLE 9

Detection of endophyte alkaloids for endophyte infected TACBOW lines

| Endophyte | Host | Plant part sampled | n | Ergovaline (μg/g) | Chanoclavine (μg/g) | Peramine (μg/g) | Cyclo (Pro, Arg) (μg/g) | Total Lolines (μg/g) | Dahurelmusin A ‡ | Paspaline * | Paxitriol * | Terpendole E * |
|---|---|---|---|---|---|---|---|---|---|---|---|---|
| AR3002 | TACBOW0045 | Tiller (dead) | 1 | ND | 0.11 | ND | — | ND | 542633 | 0.001 | ND | 0.001 |
| AR3002 | TACBOW0045 | Tiller (dead) | 1 | ND | 0.03 | ND | — | ND | 1004740 | 0.001 | ND | 0.001 |
| AR3002 | TACBOW0054 | Tiller (dead) | 1 | ND | 0.03 | ND | — | ND | 27109 | ND | ND | ND |
| AR3002 | TACBOW0059 | Tiller (dead) | 1 | ND | 0.09 | ND | — | ND | 229742 | ND | ND | 0.001 |
| AR3002 | TACBOW0059 | Tiller (dead) | 1 | ND | 0.09 | ND | — | ND | 156416 | ND | ND | ND |
| AR3002 | TACBOW0011 | Tiller | 37 | ND | 0.23 (0.04) | ND | ND | ND | 4786814 (423046) | 0.025 (0.002) | ND | 0.042 (0.004) |
| AR3002 | TACBOW0011 | Straw | 1 | ND | 0.5 | ND | ND | ND | 558410 | 0.03 | ND | 0.03 |
| AR3002 | TACBOW0011 | Seed head | 1 | ND | 0.9 | ND | ND | ND | 1547799 | 0.06 | ND | 0.04 |
| AR3002 | TACBOW0244 | Tiller (dead) | 1 | ND | 0.14 | ND | — | ND | 112787 | ND | ND | ND |
| AR3002 | TACBOW0260 | Tiller (dead) | 1 | ND | 0.14 | ND | — | ND | 419547 | 0.003 | ND | 0.004 |
| AR3002 | TACBOW0261 | Tiller (dead) | 1 | ND | 0.19 | ND | — | ND | 102628 | 0.001 | ND | 0.001 |
| AR3002 | TACBOW0272 | Tiller (dead) | 1 | ND | 0.13 | ND | — | ND | 1029636 | 0.001 | ND | 0.002 |
| AR3013 | TACBOW0011 | Tiller | 3 | ND | ND | ND | — | ND | ND | 0.020 (0.006) | 0.140 (0.071) | 0.059 (0.037) |
| AR3060 | TACBOW0011 | Seed | 1 | 2.5 | 0.1 | ND | ND | ND | — | ND | ND | ND |
| AR3060 | TACBOW0011 | Tiller | 10 | 5.86 (0.85) | 1.21 (0.13) | ND | | ND | — | — | — | — |
| AR3060 | TACBOW0011 | Leaf | 2 | 4.74 (0.12) | 1.67 (0.09) | ND | ND | ND | — | ND | ND | ND |
| AR3060 | TACBOW0011 | Straw | 4 | 8.2 (0.6) | — | — | — | — | — | — | — | — |
| AR3060 | TACBOW0018 | Leaf | 3 | 3.36 (1.04) | 2.22 (0.87) | ND | ND | ND | — | ND | ND | ND |
| AR3070 | TACBOW0011 | Leaf | 1 | ND | ND | 49.4 | ND | ND | — | ND | ND | ND |
| AR3070 | TACBOW0011 | Tiller | 9 | ND | ND | 171.5 (10.1) | ND | ND | ND | ND | ND | ND |

‡ Dahurelmusin A reported as area under the curve
* Paspaline, paxitriol, and terpendole E reported as Paxilline equivalents units.
"ND" = not detected, "—" = sample was not analysed for this alkaloid.
Where multiple samples were analysed (n > 1), the value given is the mean, with the numbers in brackets referring to standard error of the mean.

or bored a hole through the growing point at the tiller base. Endophyte status was rechecked by blotting one tiller per plant.

Adult feeding, oviposition and larval damage data were analysed by analysis of variance. The number of eggs was log transformed (Log+1) for analysis. Because the number of tillers differed significantly between treatments this was used as a covariate in the analysis of adult feeding and oviposition. Similarly, the number of eggs laid was used as a covariate for analysis of the percentage of tillers with all levels of larval damage, and the percentage with moderate and severe damage (scores 2 and 3 combined).

Results:

Argentine stem weevil adult feeding was significantly reduced by endophyte AR3070 (P=0.001) compared with endophyte-free plants (Table 10). AR3070 had fewer eggs/plant than AR3002 (P=0.055) but the number of eggs did not differ from endophyte-free or AR3060.

AR3070 had a significantly lower percentage of tillers with all levels of damage compared with the endophyte-free control (P=0.012) but differences between the control and AR3002 and AR3060 were not significant (P>0.05) (Table 10). Taking only those that were moderately and severely damaged (i.e. excluding those with minor damage), all three endophytes significantly reduced the amount of damage (P=0.002) compared with the endophyte-free treatment.

TABLE 10

Number of Argentine stem weevil adult feeding scars and eggs and the percentage of tillers with all levels of larval damage (Total) and with moderate and severe damage on TACBOW0011 plants infected with three different endophyte strains and an endophyte-free control. SED = standard error of the difference.

| | Endophyte Treatment | | | | |
| --- | --- | --- | --- | --- | --- |
| | Nil | AR3002 | AR3060 | AR3070 | SED |
| Adult FS/plant | 165 | 114 | 198 | 45 | 40.5 |
| Eggs (Log N + 1)/plant | 0.90 | 1.51 | 1.12 | 0.19 | 0.459 |
| Total Larval Damage (%) | 48.5 | 32.7 | 32.0 | 18.3 | 8.38 |
| Moderate and severe damage (%) | 43.2 | 12.9 | 11.0 | 13.8 | 8.83 |

Although the invention has been described by way of example and with reference to particular embodiments, it is to be understood that modifications and/or improvements may be made without departing from the scope of the invention.

In addition, where features or aspects of the invention are described in terms of Markush groups, those skilled in the art will recognise that the invention is also thereby described in terms of any individual member or subgroup of members of the Markush group.

INDUSTRIAL APPLICATION

The *Epichloë* endophyte strains, plant/fungal symbioses, seeds produced from such symbioses and methods of making such symbioses and methods of identifying stable symbiotic associations according to the invention as disclosed herein all have industrial application for the production of plants that are used for human or animal consumption.

REFERENCES

1. *"Crops/World Total/Wheat/Area Harvested/*2014 (pick list)". United Nations, Food and Agriculture Organization, Statistics Division (FAOSTAT). 2014. Retrieved 8 Dec. 2016.
2. *"World food situation: FAO cereal supply and demand brief"*. Rome, Italy: United Nations, Food and Agriculture Organization. 8 Dec. 2016. Retrieved 14 Dec. 2016.
3. Casida J E, Quistad G B (1998) Golden Age of Insecticide Research: Past, Present, or Future? Annual Review of Entomology 43: 1-16.
4. Zejda J E, McDuffie H H, Dosman J A (1993) Epidemiology of health and safety risks in agriculture and related industries-Practical applications for rural physicians. Western Journal of Medicine 158: 56-63.
5. Zhang, D X, Nagabhyru P, Blankenship J D, Schardl C L (2010) Are loline alkaloid levels regulated in grass endophytes by gene expression or substrate availability? Plant Signaling and Behavior 5 (11); 1419-22.
6. Koulman A, Lane G A, Christensen M J, Fraser K, Tapper B A (2007) Peramine and other fungal alkaloids are exuded in the guttation fluid of endophyte-infected grasses. Phytochemistry 68: 355-360.
7. Tsai H F, Liu J S, Staben C, Christensen M J, Latch G C, Siegel M R, Schardl C L (1994). Evolutionary diversification of fungal endophytes of tall fescue grass by hybridization with *Epichloë* species. Proc. Natl. Acad. Sci. USA 91 (7); 2542-2546.
8. Moon C D, Craven K D, Leuchtmann A, Clements S L, Schardl C L (2004). Prevalence of interspecific hybrids amongst asexual fungal endophytes of grasses. Molecular Ecology 13 (6); 1455-1467.
9. Glenn A E, Bacon C W, Price R, Hanlin R T (1996) Molecular phylogeny of Acremonium and its taxonomic implications. Mycologia 88: 369-383.
10. Miller J S, Funk V A, Wagner W L, Barrie F, Hoch P C, Herendeen P (2011) Outcomes of the 2011 botanical nomenclature section at the XVIII International Botanical Congress. PhytoKeys 5: 1-3.
11. Schardl C L, Craven K D, Speakman S, Stromberg A, Lindstrom A, Yoshida R (2008). A novel test for host-symbiont codivergence indicates ancient origin of fungal endophytes in grasses. Syst Biol. 57: 483-498.
12. Marshall D, Tunali B, Nelson L R (1999) Occurrence of fungal endophytes in species of wild triticum. Crop Science 39: 1507-1512.
13. Welty R E, Azevedo M D, Cooper T M (1987) Influence of moisture content, temperature, and length of storage on seed germination and survival of endophytic fungi in seeds of tall fescue and perennial ryegrass. Phytopathology 77: 893-900.
14. Simpson W R, Mace W J (2012) Novel associations between Epichloë endophytes and grasses: Possibilities and outcomes. In 'Epichloë, endophytes of cool season grasses: Implications, utilization and biology.' (Eds C A Young, G E Aiken, R L McCulley, J R Strickland, C L Schardl) pp. 35-39. (The Samuel Roberts Noble Foundation: Ardmore, Oklahoma).

15. Christensen M J, Simpson W R, Al Samarrai T (2000) Infection of tall fescue and perennial ryegrass plants by combinations of different Neotyphodium endophytes. Mycological Research 104: 974-978.
16. Christensen M J, Bennett R J, Schmid J (2002) Growth of Epichloë/Neotyphodium and p-endophytes in leaves of Lolium and Festuca grasses. Mycological Research 106: 93-106.
17. Christensen M J, Saulsbury K, Simpson W R (2012) Conspicuous epiphytic growth of an interspecific hybrid *Neotyphodium* sp. endophyte on distorted host inflorescences. Fungal Biology 116: 42-48.
18. Christensen M J, Bennett R J, Schmid J (2001) Vascular bundle colonisation by Neotyphodium endophytes in natural and novel associations with grasses. Mycological Research 105: 1239-1245.
19. Christensen M J (1995) Variation in the ability of Acremonium endophytes of *Lolium perenne, Festuca arundinacea* and *F. pratensis* to form compatible associations in the 3 grasses. Mycological Research 99: 466-470.
20. Schardl C L, Grossman R B, Nagabhyru P, Faulkner J R, Mallik U P (2007) Loline alkaloids: Currencies of mutualism. Phytochemistry 68: 980-996.
21. Schardl C L, Young C A, Faulkner J R, Florea S, Pan J (2012) Chemotypic diversity of Epichloë fungal symbionts of grasses. Fungal Ecology 5: 331-344.
22. Bush L P, Wilkinson H H, Schardl C L (1997) Bioprotective Alkaloids of Grass-Fungal Endophyte Symbioses. Plant Physiology 114: 1-7.
23. Malinowski D P, Belesky D P (2000) Adaptations of endophyte-infected cool-season grasses to environmental stresses: Mechanisms of drought and mineral stress tolerance. Crop Science: 40: 923-940.
24. Porter J K (1994). Chemical constituents of grass endophytes. In: Bacon, C. W., White Jr., J. F (Eds), Biotechnology of Endophytic Fungi of Grasses. CRC, Boca Raton, FL, pp. 103-123.
25. Blankenship J D, Spiering M J, Wilkinson H H, Fannin F F, Bush L P, Schardl C L (2001). Production of loline alkaloids by the grass endophyte, *Neotyphodium uncinatum*, in defined media. Phytochemistry 58: 395-401.
26. Tanaka A, Tapper B A, Popay A, Parker E J, Scott B (2005) A symbiosis expressed non-ribosomal peptide synthetase from a mutualistic fungal endophyte of perennial ryegrass confers protection to the symbiotum from insect herbivory. Molecular Microbiology 57: 1036-1050.
27. Rowan D D, Latch G C M (1994) Utilization of endophyte-infected perennial ryegrasses for increased insect resistance. In: Bacon C W, White Jr. J F (eds), Biotechnology of Endophyte Fungi of Grasses. CRC Press, Boca Raton, Forida, pp. 169-183.
28. Latch G C M, Christensen M J (1985) Artificial Infection of Grasses with Endophytes. Annals of Applied Biology 107: 17-24.
29. SIMPSON, W. R., FAVILLE, M. J., MORAGA, R. A., WILLIAMS, W. M., MCMANUS, M. T. and JOHNSON, R. D. (2014), Epichloë fungal endophytes and the formation of synthetic symbioses in Hordeeae (=Triticeae) grasses. Jnl of Systematics Evolution, 52: 794-806. doi: 10.1111/jse.12107.
30. Leuchtmann A, C W Bacon, C L Schardl, J F White and M Tadych. 2014. Nomenclatural realignment of *Neotyphodium* species with genus Epichloë. Mycologia 106: 202-215.

DESCRIPTION OF THE MICROORGANISM DEPOSITS MADE UNDER THE BUDAPEST TREATY

The following biological deposits have been made under the terms of the Budapest Treaty on the International Recognition of the Deposit of Micro-organisms for the Purposes of Patent Procedure

| Deposit Identification Reference | International Depository Designation | Date of Deposit |
|---|---|---|
| AR3002 | NRRL 50579 | 13 October 2011 |
| AR3013 | NRRL 67557 | 5 February 2018 |
| AR3060 | NRRL 67592 | 5 February 2018 |
| AR3067 | NRRL 50719 | 6 March 2012 |
| AR3070 | NRRL 67564 | 5 February 2018 |
| AR3108 | NRRL 67572 | 5 February 2018 |

Certificates of Deposit and Statements of Viability for the above deposited micro-organisms are appended.

DESCRIPTION OF THE MICROORGANISM DEPOSITS MADE UNDER THE BUDAPEST TREATY

The following biological deposits have been made under the terms of the Budapest Treaty on the International Recognition of the Deposit of Micro-organisms for the Purposes of Patent Procedure

| Wheat Deposit Identification Reference | International Depository Designation | Date of Deposit |
|---|---|---|
| TACBOW0003 | KCTC 15349BP | 10 March 2023 |
| TACBOW0005 | KCTC 15350BP | 10 March 2023 |
| TACBOW0010 | KCTC 15351BP | 10 March 2023 |
| TACBOW0011 | KCTC 15352BP | 10 March 2023 |
| TACBOW0018 | KCTC 15353BP | 10 March 2023 |
| TACBOW0028 | KCTC 15354BP | 10 March 2023 |
| TACBOW0044 | KCTC 15355BP | 10 March 2023 |
| TACBOW0045 | KCTC 15356BP | 10 March 2023 |
| TACBOW0054 | KCTC 15357BP | 10 March 2023 |
| TACBOW0059 | KCTC 15358BP | 10 March 2023 |
| TACBOW0067 | KCTC 15359BP | 10 March 2023 |
| TACBOW0128 | KCTC 15360BP | 10 March 2023 |
| TACBOW0209 | KCTC 15361BP | 10 March 2023 |
| TACBOW0221 | KCTC 15362BP | 10 March 2023 |
| TACBOW0226 | KCTC 15363BP | 10 March 2023 |
| TACBOW0236 | KCTC 15364BP | 10 March 2023 |
| TACBOW0237 | KCTC 15365BP | 10 March 2023 |
| TACBOW0244 | KCTC 15366BP | 10 March 2023 |
| TACBOW0260 | KCTC 15367BP | 10 March 2023 |

| TACBOW0261 | KCTC 15368BP | 10 March 2023 |
| TACBOW0272 | KCTC 15369BP | 10 March 2023 |
| TACBOW0275 | KCTC 15370BP | 10 March 2023 |

Certificates of Deposit and Statements of Viability for the above deposited microorganisms are appended.

The invention claimed is:

1. A method of identifying a wheat plant that forms a stable symbiotic combination with a fungal endophyte comprising
artificially inoculating a fungal endophyte into a candidate wheat plant to form a wheat plant/endophyte combination,
propagating the wheat plant/endophyte combination,
obtaining seed from the propagated combination, and identifying the presence of the endophyte in the seed, and
selecting the wheat plant that is capable of forming a stable symbiotic combination with the fungal endophyte, wherein the fungal endophyte is an isolated strain of *Epichloë* fungal endophyte selected from the group consisting of AR3002 (NRRL #50579), AR3013 (NRRL #67557), AR3067 (NRRL #50719), AR3070 (NRRL #67564), and AR3108 (NRRL #67572).

2. A method of making a stable symbiotic combination comprising a wheat plant and an *Epichloë* fungal endophyte comprising
artificially inoculating an *Epichloë* fungal endophyte into a candidate wheat plant to form a wheat plant/endophyte combination,
propagating the wheat plant/endophyte combination,
obtaining seed from the propagated combination, and
identifying the presence of the *Epichloë* endophyte in the seed, and
selecting a stable symbiotic combination comprising the wheat plant and the *Epichloë* fungal endophyte, wherein the fungal endophyte is an isolated strain of *Epichloë* fungal endophyte selected from the group consisting of AR3002 (NRRL #50579), AR3013 (NRRL #67557), AR3067 (NRRL #50719), AR3070 (NRRL #67564), and AR3108 (NRRL #67572).

3. The method of claim 2, wherein the fungal endophyte is isolated from *Elymus* spp.

4. The method of claim 2, wherein the fungal endophyte is an *Epichloë* fungal endophyte isolated from wild cereal grasses selected from the group consisting of *Elymus* species grasses and *Hordeum* species grasses.

5. The method of claim 2, wherein the wheat plant is a plant from a line obtained from the Tottori Alien Chromosome Bank of Wheat (TACBOW) selected from the group consisting of TACBOW0003 (KCTC 15349BP), TACBOW0005 (KCTC 15350BP), TACBOW0010 (KCTC 15351BP), TACBOW0011 (KCTC 15352BP), TACBOW0018 (KCTC 15353BP), TACBOW0028 (KCTC 15354BP), TACBOW0044 (KCTC 15355BP), TACBOW0045 (KCTC 15356BP), TACBOW0054 (KCTC 15357BP), TACBOW0059 (KCTC 15358BP), TACBOW0067 (KCTC 15359BP), TACBOW0128 (KCTC 15360BP), TACBOW0209 (KCTC 15361BP), TACBOW0221 (KCTC 15362BP), TACBOW0226 (KCTC 15363BP), TACBOW0236 (KCTC 15364BP), TACBOW237 (KCTC 15365BP), TACBOW0244 (KCTC 15366BP), TACBOW0260 (KCTC 15367BP), TACBOW0261 (KCTC 15368BP), TACBOW0272 (KCTC 15369BP), and TACBOW0275 (KCTC 15370BP).

6. The method of claim 2, wherein the wheat plant in the combination shows a normal morphological phenotype.

7. The method of claim 2, the wheat plant in the combination has a tall floral phenotype that produces seed containing the endophyte.

8. The method of claim 2, wherein the wheat plant in the combination produces seed that is viable, wherein the seed will germinate to form a next generation of the combination.

9. The method of claim 2, wherein the wheat plant/endophyte combination produces an alkaloid that confers at least some level of pest protection or resistance, or disease protection or resistance, on the combination, wherein the alkaloid is selected from the group consisting of lolines, peramine, indole diterpene alkaloids and ergot alkaloids.

10. A stable symbiotic combination comprising an isolated strain of *Epichloë* fungal endophyte selected from the group consisting of AR3002 (NRRL #50579), AR3013 (NRRL #67557), AR3067 (NRRL #50719), AR3070 (NRRL #67564) and AR3108 (NRRL #67572), and a wheat plant.

11. The combination of claim 10, wherein the wheat plant in the combination shows a normal morphological phenotype.

12. The combination of claim 10, wherein the wheat plant shows a tall floral phenotype that produces seed containing the endophyte.

13. The combination of claim 10, wherein the wheat plant produces seed that is viable, wherein the seed will germinate to form a next generation of the combination.

* * * * *

SEQUENCE LISTING

```
Sequence total quantity: 46
SEQ ID NO: 1              moltype = DNA   length = 18
FEATURE                   Location/Qualifiers
misc_feature              1..18
                          note = Primer
source                    1..18
                          mol_type = other DNA
                          organism = synthetic construct
SEQUENCE: 1
tgtaaaacga cggccagt                                                  18

SEQ ID NO: 2              moltype =    length =
SEQUENCE: 2
000

SEQ ID NO: 3              moltype = DNA   length = 24
FEATURE                   Location/Qualifiers
misc_feature              1..24
                          note = Primer
source                    1..24
                          mol_type = other DNA
                          organism = synthetic construct
SEQUENCE: 3
cgctcagggc tacatacacc atgg                                           24

SEQ ID NO: 4              moltype = DNA   length = 23
FEATURE                   Location/Qualifiers
misc_feature              1..23
                          note = Primer
source                    1..23
                          mol_type = other DNA
                          organism = synthetic construct
SEQUENCE: 4
ctcatcgagt aacgcaggcg acg                                            23

SEQ ID NO: 5              moltype = DNA   length = 24
FEATURE                   Location/Qualifiers
misc_feature              1..24
                          note = Primer
source                    1..24
                          mol_type = other DNA
                          organism = synthetic construct
SEQUENCE: 5
catggatgga caagagattg cacg                                           24

SEQ ID NO: 6              moltype = DNA   length = 24
FEATURE                   Location/Qualifiers
misc_feature              1..24
                          note = Primer
source                    1..24
                          mol_type = other DNA
                          organism = synthetic construct
SEQUENCE: 6
ttcactgcta caattctgtc cagc                                           24

SEQ ID NO: 7              moltype = DNA   length = 21
FEATURE                   Location/Qualifiers
misc_feature              1..21
                          note = Primer
source                    1..21
                          mol_type = other DNA
                          organism = synthetic construct
SEQUENCE: 7
cacaaagaca aacgccaaaa g                                              21

SEQ ID NO: 8              moltype = DNA   length = 22
FEATURE                   Location/Qualifiers
misc_feature              1..22
                          note = Primer
source                    1..22
                          mol_type = other DNA
                          organism = synthetic construct
SEQUENCE: 8
gcaaagctca cagacaaagg tc                                             22

SEQ ID NO: 9              moltype = DNA   length = 21
FEATURE                   Location/Qualifiers
misc_feature              1..21
```

```
                        note = Primer
source                  1..21
                        mol_type = other DNA
                        organism = synthetic construct
SEQUENCE: 9
tacctctgca cggtgtattc c                                                  21

SEQ ID NO: 10           moltype = DNA   length = 24
FEATURE                 Location/Qualifiers
misc_feature            1..24
                        note = Primer
source                  1..24
                        mol_type = other DNA
                        organism = synthetic construct
SEQUENCE: 10
tgcataacac tcaccttata gtcg                                               24

SEQ ID NO: 11           moltype = DNA   length = 22
FEATURE                 Location/Qualifiers
misc_feature            1..22
                        note = Primer
source                  1..22
                        mol_type = other DNA
                        organism = synthetic construct
SEQUENCE: 11
gcgttgagga ggctagatag aa                                                 22

SEQ ID NO: 12           moltype = DNA   length = 22
FEATURE                 Location/Qualifiers
misc_feature            1..22
                        note = Primer
source                  1..22
                        mol_type = other DNA
                        organism = synthetic construct
SEQUENCE: 12
ttccaagctg aacaaaagtc aa                                                 22

SEQ ID NO: 13           moltype = DNA   length = 22
FEATURE                 Location/Qualifiers
misc_feature            1..22
                        note = Primer
source                  1..22
                        mol_type = other DNA
                        organism = synthetic construct
SEQUENCE: 13
atttgcagca gagatgatgt gt                                                 22

SEQ ID NO: 14           moltype = DNA   length = 22
FEATURE                 Location/Qualifiers
misc_feature            1..22
                        note = Primer
source                  1..22
                        mol_type = other DNA
                        organism = synthetic construct
SEQUENCE: 14
cctgcaccgg actgttagta at                                                 22

SEQ ID NO: 15           moltype = DNA   length = 24
FEATURE                 Location/Qualifiers
misc_feature            1..24
                        note = Primer
source                  1..24
                        mol_type = other DNA
                        organism = synthetic construct
SEQUENCE: 15
gatgacgtat cttgatgcta ccac                                               24

SEQ ID NO: 16           moltype = DNA   length = 24
FEATURE                 Location/Qualifiers
misc_feature            1..24
                        note = Primer
source                  1..24
                        mol_type = other DNA
                        organism = synthetic construct
SEQUENCE: 16
cgtgtataaa gttcgggatc ctat                                               24

SEQ ID NO: 17           moltype = DNA   length = 24
FEATURE                 Location/Qualifiers
```

```
                             -continued misc_feature              1..24
                          note = Primer
source                    1..24
                          mol_type = other DNA
                          organism = synthetic construct
SEQUENCE: 17
gagatatccc gtctcctgat ctaa                                              24

SEQ ID NO: 18             moltype = DNA   length = 24
FEATURE                   Location/Qualifiers
misc_feature              1..24
                          note = Primer
source                    1..24
                          mol_type = other DNA
                          organism = synthetic construct
SEQUENCE: 18
cacagcgtta cactatcaac ttcc                                              24

SEQ ID NO: 19             moltype = DNA   length = 24
FEATURE                   Location/Qualifiers
misc_feature              1..24
                          note = Primer
source                    1..24
                          mol_type = other DNA
                          organism = synthetic construct
SEQUENCE: 19
cactaaacac acccaagaac aaga                                              24

SEQ ID NO: 20             moltype = DNA   length = 24
FEATURE                   Location/Qualifiers
misc_feature              1..24
                          note = Primer
source                    1..24
                          mol_type = other DNA
                          organism = synthetic construct
SEQUENCE: 20
agacaggtaa gaagttttcc cctt                                              24

SEQ ID NO: 21             moltype = DNA   length = 24
FEATURE                   Location/Qualifiers
misc_feature              1..24
                          note = Primer
source                    1..24
                          mol_type = other DNA
                          organism = synthetic construct
SEQUENCE: 21
agcttttcca tgacgacata cata                                              24

SEQ ID NO: 22             moltype = DNA   length = 24
FEATURE                   Location/Qualifiers
misc_feature              1..24
                          note = Primer
source                    1..24
                          mol_type = other DNA
                          organism = synthetic construct
SEQUENCE: 22
taatttaggg tagcattttc tccg                                              24

SEQ ID NO: 23             moltype = DNA   length = 24
FEATURE                   Location/Qualifiers
misc_feature              1..24
                          note = Primer
source                    1..24
                          mol_type = other DNA
                          organism = synthetic construct
SEQUENCE: 23
ggtccctatt ctaatgcagg tatg                                              24

SEQ ID NO: 24             moltype = DNA   length = 24
FEATURE                   Location/Qualifiers
misc_feature              1..24
                          note = Primer
source                    1..24
                          mol_type = other DNA
                          organism = synthetic construct
SEQUENCE: 24
cagtgtacgg gactttgtca atac                                              24

SEQ ID NO: 25             moltype = DNA   length = 24
```

-continued

```
FEATURE                 Location/Qualifiers
misc_feature            1..24
                        note = Primer
source                  1..24
                        mol_type = other DNA
                        organism = synthetic construct
SEQUENCE: 25
tgtataataa acatggcgtg ctct                                          24

SEQ ID NO: 26           moltype = DNA  length = 24
FEATURE                 Location/Qualifiers
misc_feature            1..24
                        note = Primer
source                  1..24
                        mol_type = other DNA
                        organism = synthetic construct
SEQUENCE: 26
gtgttgaaag ttgttggatc actc                                          24

SEQ ID NO: 27           moltype = DNA  length = 24
FEATURE                 Location/Qualifiers
misc_feature            1..24
                        note = Primer
source                  1..24
                        mol_type = other DNA
                        organism = synthetic construct
SEQUENCE: 27
cgaaattgta gactatgttg gagc                                          24

SEQ ID NO: 28           moltype = DNA  length = 24
FEATURE                 Location/Qualifiers
misc_feature            1..24
                        note = Primer
source                  1..24
                        mol_type = other DNA
                        organism = synthetic construct
SEQUENCE: 28
gtagatgtat tttgagcagg gctt                                          24

SEQ ID NO: 29           moltype = DNA  length = 24
FEATURE                 Location/Qualifiers
misc_feature            1..24
                        note = Primer
source                  1..24
                        mol_type = other DNA
                        organism = synthetic construct
SEQUENCE: 29
gagtgagacc cggtgtagta agtc                                          24

SEQ ID NO: 30           moltype = DNA  length = 24
FEATURE                 Location/Qualifiers
misc_feature            1..24
                        note = Primer
source                  1..24
                        mol_type = other DNA
                        organism = synthetic construct
SEQUENCE: 30
gagtcattct tcgtccattg tctt                                          24

SEQ ID NO: 31           moltype = DNA  length = 24
FEATURE                 Location/Qualifiers
misc_feature            1..24
                        note = Primer
source                  1..24
                        mol_type = other DNA
                        organism = synthetic construct
SEQUENCE: 31
gaaatgaggc gtctatctta aagc                                          24

SEQ ID NO: 32           moltype = DNA  length = 24
FEATURE                 Location/Qualifiers
misc_feature            1..24
                        note = Primer
source                  1..24
                        mol_type = other DNA
                        organism = synthetic construct
SEQUENCE: 32
tttcttgatt tccaaagaac aaca                                          24
```

-continued

```
SEQ ID NO: 33              moltype = DNA   length = 24
FEATURE                    Location/Qualifiers
misc_feature               1..24
                           note = Primer
source                     1..24
                           mol_type = other DNA
                           organism = synthetic construct
SEQUENCE: 33
cagtcatcga ttaaaagtga gcat                                              24

SEQ ID NO: 34              moltype = DNA   length = 24
FEATURE                    Location/Qualifiers
misc_feature               1..24
                           note = Primer
source                     1..24
                           mol_type = other DNA
                           organism = synthetic construct
SEQUENCE: 34
atgtcatctg cttcaacaag agtc                                              24

SEQ ID NO: 35              moltype = DNA   length = 24
FEATURE                    Location/Qualifiers
misc_feature               1..24
                           note = Primer
source                     1..24
                           mol_type = other DNA
                           organism = synthetic construct
SEQUENCE: 35
tcttccatac aatttcttcc cttc                                              24

SEQ ID NO: 36              moltype = DNA   length = 24
FEATURE                    Location/Qualifiers
misc_feature               1..24
                           note = Primer
source                     1..24
                           mol_type = other DNA
                           organism = synthetic construct
SEQUENCE: 36
actagtcaat agcacaaatt gcca                                              24

SEQ ID NO: 37              moltype = DNA   length = 24
FEATURE                    Location/Qualifiers
misc_feature               1..24
                           note = Primer
source                     1..24
                           mol_type = other DNA
                           organism = synthetic construct
SEQUENCE: 37
agccctagcc tatacatctt tcct                                              24

SEQ ID NO: 38              moltype = DNA   length = 24
FEATURE                    Location/Qualifiers
misc_feature               1..24
                           note = Primer
source                     1..24
                           mol_type = other DNA
                           organism = synthetic construct
SEQUENCE: 38
aatgggcttt tccattcaat aata                                              24

SEQ ID NO: 39              moltype = DNA   length = 24
FEATURE                    Location/Qualifiers
misc_feature               1..24
                           note = Primer
source                     1..24
                           mol_type = other DNA
                           organism = synthetic construct
SEQUENCE: 39
aaatgattgt tcgctgtatg ctaa                                              24

SEQ ID NO: 40              moltype = DNA   length = 24
FEATURE                    Location/Qualifiers
misc_feature               1..24
                           note = Primer
source                     1..24
                           mol_type = other DNA
                           organism = synthetic construct
SEQUENCE: 40
atgtcatgtt tgattccatt tttg                                              24
```

```
SEQ ID NO: 41          moltype = DNA  length = 24
FEATURE                Location/Qualifiers
misc_feature           1..24
                       note = Primer
source                 1..24
                       mol_type = other DNA
                       organism = synthetic construct
SEQUENCE: 41
ctgctagaca tacttggaac atgg                                           24

SEQ ID NO: 42          moltype = DNA  length = 24
FEATURE                Location/Qualifiers
misc_feature           1..24
                       note = Primer
source                 1..24
                       mol_type = other DNA
                       organism = synthetic construct
SEQUENCE: 42
cagtcgaata atttagggag catt                                           24

SEQ ID NO: 43          moltype = DNA  length = 24
FEATURE                Location/Qualifiers
misc_feature           1..24
                       note = Primer
source                 1..24
                       mol_type = other DNA
                       organism = synthetic construct
SEQUENCE: 43
actgagtgat ggtagaaaag aggg                                           24

SEQ ID NO: 44          moltype = DNA  length = 24
FEATURE                Location/Qualifiers
misc_feature           1..24
                       note = Primer
source                 1..24
                       mol_type = other DNA
                       organism = synthetic construct
SEQUENCE: 44
cagaatttct cccatatata cgcc                                           24

SEQ ID NO: 45          moltype = DNA  length = 24
FEATURE                Location/Qualifiers
misc_feature           1..24
                       note = Primer
source                 1..24
                       mol_type = other DNA
                       organism = synthetic construct
SEQUENCE: 45
tcatctcttc aagactttcc tcct                                           24

SEQ ID NO: 46          moltype = DNA  length = 24
FEATURE                Location/Qualifiers
misc_feature           1..24
                       note = Primer
source                 1..24
                       mol_type = other DNA
                       organism = synthetic construct
SEQUENCE: 46
tttagtgtca cttcttcatc tcgc                                           24
```